United States Patent
Ryono et al.

Patent Number: 4,981,843
Date of Patent: Jan. 1, 1991

[54] N-HETEROCYCLIC ALCOHOL DERIVATIVES

[75] Inventors: Denis E. Ryono, Princeton; Harold N. Weller, III, Pennington, both of N.J.

[73] Assignee: E. R. Squibb & Sons, Inc., Princeton, N.J.

[21] Appl. No.: 178,948

[22] Filed: Apr. 7, 1988

[51] Int. Cl.$^5$ .................. A61K 37/43; C07K 5/08
[52] U.S. Cl. ................................ 514/18; 514/19; 530/323; 530/331; 530/332; 530/800
[58] Field of Search ............... 548/204; 514/365, 18; 530/331, 800

[56] References Cited

U.S. PATENT DOCUMENTS 4,629,724 12/1986 Ryono et al. .................. 514/18
4,668,769 5/1987 Hoover ........................... 530/331

FOREIGN PATENT DOCUMENTS 5288186 12/1985 Australia .
0104041 3/1984 European Pat. Off. .
0190891 8/1986 European Pat. Off. .
201036 4/1986 Japan .

OTHER PUBLICATIONS

Powers et al., "Inhibition of Human Leukocyte Elastase, Porcine Pancreatic Elastase and Cathepsin G by Peptide Ketones", Proceedings from the 9th American Peptide Symposium, Jun. 23-28, 1985, Univ. of Toronto, Canada.

*Primary Examiner*—Glennon H. Hollrah
*Assistant Examiner*—Susan P. Treanor
*Attorney, Agent, or Firm*—T. R. Furman, Jr.

[57] ABSTRACT

Compounds of the formula

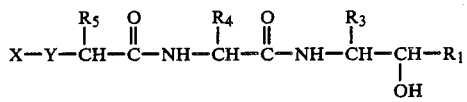

wherein $R_1$ is an N-heterocyclic group as defined herein and Y can be —NH—, —O— or —CH$_2$—, are disclosed. These compounds are inhibitors of renin and therefore useful as cardiovascular agents.

12 Claims, No Drawings

N-HETEROCYCLIC ALCOHOL DERIVATIVES

BACKGROUND OF THE INVENTION

Jones et al. in WO 84/03044 disclose renin inhibiting tetra-, penta-, or hexapeptide analogues of the formula

where X and W are terminal groups; D, E, B and Z, of which any one or, except with reduced analogues, two may be absent, are aromatic, lipophilic or (in the case of E) aromatic, lipophilic, or basic amino acid or amino acid analogue residues, and A is an analogue of a lipophilic or aromatic dipeptide residue wherein the peptide link is replaced by one to four-atom carbon or carbon-nitrogen link which as such or in hydrated form is an unhydrolyzable tetrahedral analogue of the transition state of the peptide bond as given above. In particular, A is defined as

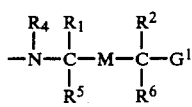

wherein M can be —CH—OH.

Szelke et al. in European patent application no. 104,041 disclose renin inhibitory polypeptides including the partial sequence

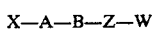

and

X-Phe-His-A-B-Z-W wherein A is

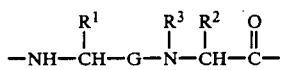

and G is

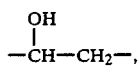

X is hydrogen, protecting group, or an amino acyl residue, B is a lipophilic amino acyl residue, and Z plus W are an amino alcohol residue or Z is aminoacyl and W is hydroxy, ester, amide, etc.

Matsueda et al. in U.S. Pat. No. 4,548,926 disclose renin inhibiting peptides of the formula

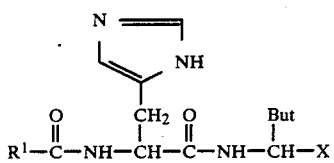

wherein But represents an isobutyl or sec-butyl group and X includes a group of the formula —CH(R$^2$)—Y.

Gordon et al. in U.S. Pat. No. 4,514,391 disclose hydroxy substituted peptide compounds of the formula

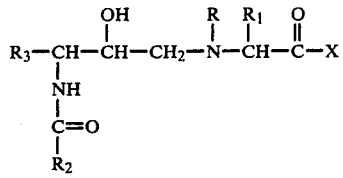

which possess angiotensin converting enzyme or enkephalinase inhibition activity.

A copending application, U.S. Ser. No. 003,446 entitled "N-HETEROCYCLIC ALCOHOL RENIN INHIBITORS", filed Jan. 15, 1987, discloses compounds of the formula

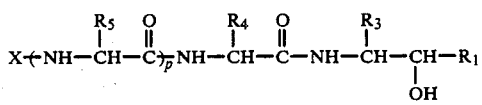

wherein R$_1$ can be various N-heterocyclic moieties.

SUMMARY OF THE INVENTION

In accordance with the present invention novel compounds which are inhibitors of renin, and therefore useful as cardiovascular agents, are disclosed. These compounds have the formula

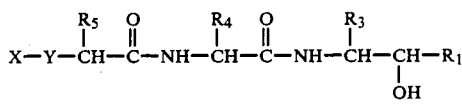

including pharmaceutically acceptable salts thereof, wherein Y can be —CH$_2$—, —NH— or —O—, provided that:

when Y is —CH$_2$—, X is

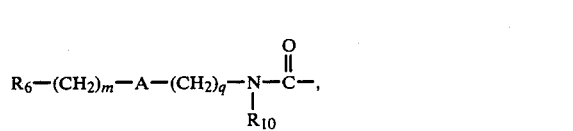

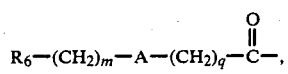

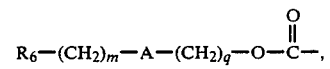

R$_6$—(CH$_2$)$_m$—A—(CH$_2$)$_q$—S—, R$_6$—(CH$_2$)$_m$—A—(CH$_2$)$_q$—SO—, R$_6$(CH$_2$)$_m$—A—(CH$_2$)$_q$—SO$_2$,

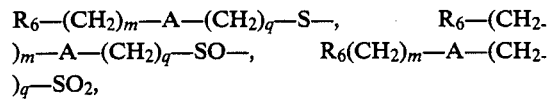

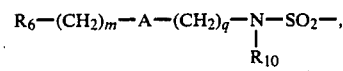

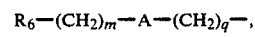

-continued

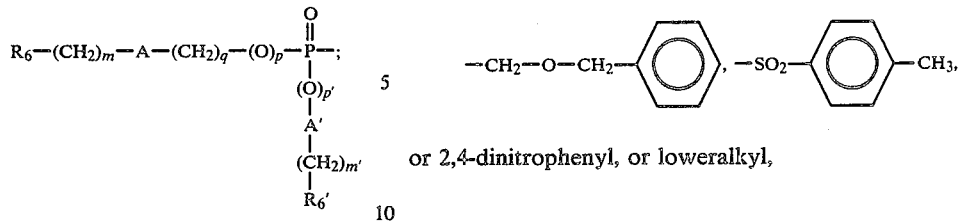

when Y is —NH—, X is

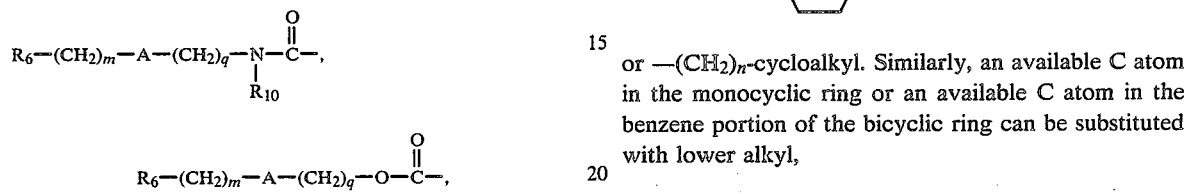

$R_6-(CH_2)_m-A-(CH_2)_q-$, $R_6-(CH_2)_m-A-(CH_2)_q-SO_2-$; and, when Y is —O—, X is

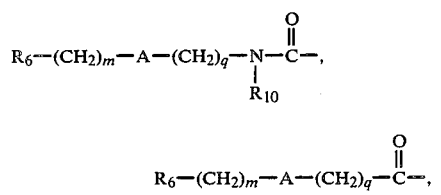

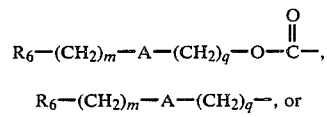

$R_6-(CH_2)_m-A-(CH_2)_q-$, or

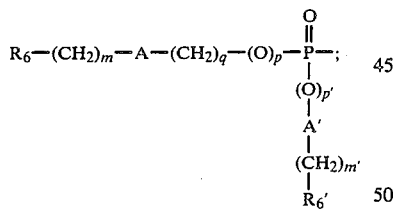

and, further wherein $R_1$ is a fully saturated, partially saturated, or unsaturated monocyclic N-heterocyclic ring of 5 or 6 atoms containing at least one N atom or a bicyclic ring in which such N-heterocyclic ring is fused to a benzene ring. The N-heterocyclic ring can also include an O or S atom or up to three additional N atoms. The N-heterocyclic ring is attached to

—CH—
|
OH by way of an available carbon atom. An available N atom in the N-heterocyclic ring can be substituted with an N-protecting group such as —CH$_2$—O—CH$_2$——SO$_2$——CH$_3$, or 2,4-dinitrophenyl, or loweralkyl, —(CH$_2$)$_n$—, or —(CH$_2$)$_n$-cycloalkyl. Similarly, an available C atom in the monocyclic ring or an available C atom in the benzene portion of the bicyclic ring can be substituted with lower alkyl, —(CH$_2$)$_n$—, or —(CH$_2$)$_n$-cycloalkyl.

Preferred N-heterocyclic rings are

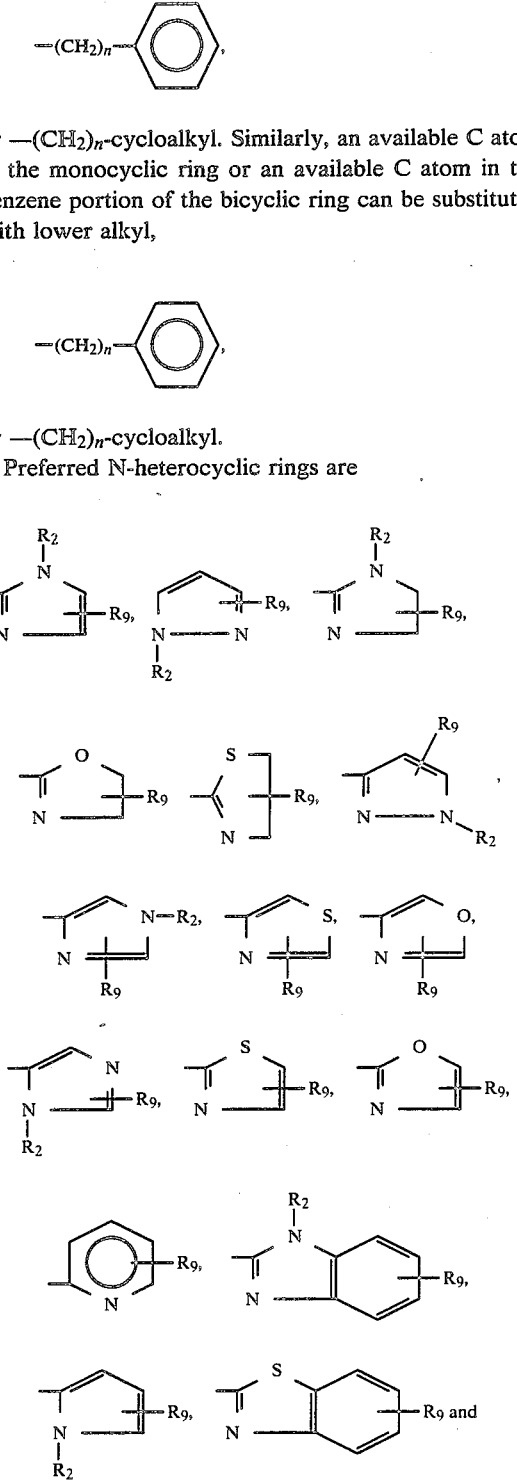

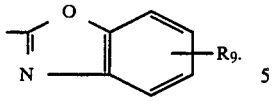

R₂ is

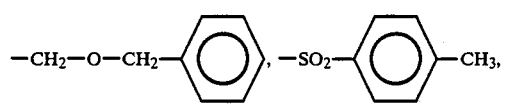

2,4-dinitrophenyl, hydrogen, lower alkyl,

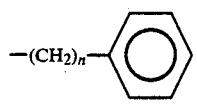

or —(CH₂)ₙ-cycloalkyl;

R₃ and R₅ are independently selected from hydrogen, lower alkyl, halo substituted lower alkyl, —(CH₂)ₙ-aryl, —(CH₂)ₙ-heterocyclo, —(CH₂)ₙ—OH, —(CH₂)ₙ—O-lower alkyl, —(CH₂)ₙ—NH₂, —(CH₂)ₙ—SH, —(CH₂)ₙ—S-lower alkyl, —(CH₂)ₙ—O—(CH₂)g—OH, —(CH₂)ₙ—O—(CH₂)g—NH₂, —(CH₂)ₙ—S—(CH₂)g—OH,

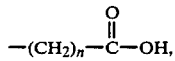

—(CH₂)ₙ—S—(CH₂)g—NH₂,

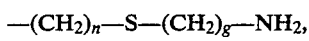

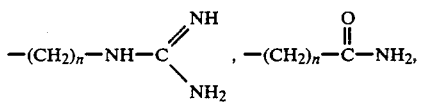

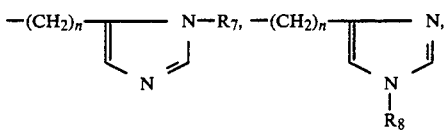

and —(CH₂)ₙ-cycloalkyl;

R₄ is selected from hydrogen, lower alkyl, halo substituted lower alkyl, —(CH₂)ₙ-aryl, —(CH₂)ₙ-heterocyclo, —(CH₂)ₙ—OH, —(CH₂)ₙ—O-lower alkyl, —(CH₂)ₙ—NH₂, —(CH₂)ₙ—SH, —(CH₂)ₙ—S-lower alkyl, —(CH₂)ₙ—O—(CH₂)g—OH, —(CH₂)ₙ—O—(CH₂)g—NH₂, —(CH₂)ₙ—S—(CH₂)g—OH,

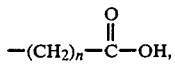

—(CH₂)ₙ—S—(CH₂)g—NH₂,

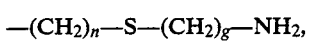

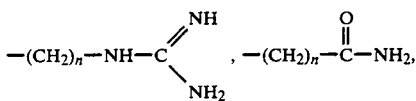

—(CH₂)ₙ-cycloalkyl,

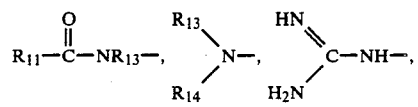

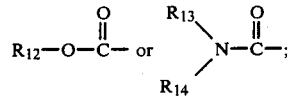

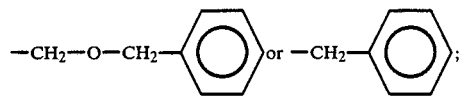

R₆ is

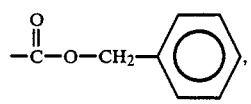

R₆′, R₆″, R₆‴, R₁₂, R₁₃ and R₁₄ are independently selected from hydrogen, alkyl, aryl, heteroaryl, arylalkyl and cycloalkyl;

m, m′, m″ and m‴ are zero or an integer from 1 to 5;
n is an integer from 1 to 5;
p and p′ are zero or 1;
g is an integer from 2 to 5;
q is an integer from 0 to 7;
R₇ is —CH₂—O—CH₂—⟨phenyl⟩ or —CH₂—⟨phenyl⟩;

R₈ is 2,4-dinitrophenyl,

—C(=O)—O—CH₂—⟨phenyl⟩,

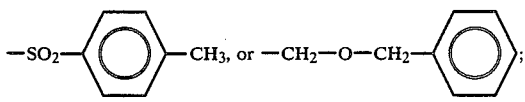

$R_9$ is hydrogen, lower alkyl,

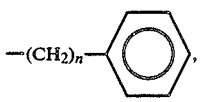

or —$(CH_2)_n$-cycloalkyl;
$R_{10}$ is —A'—$(CH_2)_{m'}$—$R_6'$;
$R_{11}$ is alkyl, alkoxy, aralkyl, aralkoxy; and,
A and A' are independently a single bond or

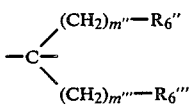

The present invention also encompasses the compounds of formula I wherein the —OH group is optionally etherified or esterified by methods known in the art.

DETAILED DESCRIPTION OF THE INVENTION

This invention in its broadest aspects relates to the compounds of formula I above, to compositions and the method of using such compounds as antihypertensive agents.

The term lower alkyl used in defining various symbols refers to straight or branched chain radicals having up to seven carbons. Similarly, the terms lower alkoxy and lower alkylthio refer to such lower alkyl groups attached to an oxygen or sulfur. The preferred lower alkyl groups are straight or branched chain of 1 to 5 carbons.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred hetero groups include 2-thiazolyl, 2- and 4-imidazolyl, 2- and 3-thienyl, 2- and 3-furyl, 2-, 3- and 4-pyridyl. The term hetero also includes bicyclic rings wherein the five or six membered ring containing O, S and N atoms as defined above is fused to a benzene ring. The preferred bicyclic ring is benzimidazolyl.

The compounds of formula I wherein Y is —$CH_2$— are prepared by coupling an amine of the formula

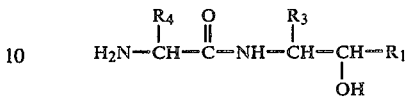

with the compound of the formula

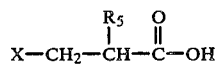

in a solvent, e.g. dimethylformamide, and in the presence of a coupling agent, e.g. dicyclohexylcarbodiimide.

To make the amine of formula II, a starting material, H—$R_1$, is treated with n-butyl lithium to obtain a compound of the formula

Compound IV is thereafter reacted with an aldehyde of the formula

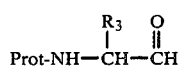

(wherein Prot is an amino protecting group, e.g. t-butoxycarbonyl) to provide the protected amine of the formula

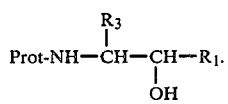

Compound VI, in a solvent such as ethyl acetate, can be deprotected by means known in the art, e.g. by treatment with hydrogen chloride, to provide an amine of the formula

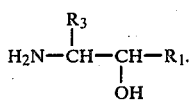

The amine of formula II can then be prepared by reacting the deprotected amine of formula VII with an N-protected amino acid of the formula

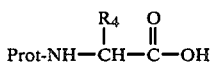

in the presence of a coupling agent, such as dicyclohexylcarbodiimide, and thereafter removing the protecting group by known means, e.g. treatment with hydrogen chloride in the case of a t-butoxycarbonyl protecting group.

To make compounds of formula I wherein Y is —$CH_2$—, X is $$R_6-(CH_2)_m-A-(CH_2)_q-\overset{\overset{O}{\|}}{C}-$$

for which $R_6$ is $$R_{11}-\overset{\overset{O}{\|}}{C}-NH-,$$

a compound of the formula $$H_2N-(CH_2)_m-A-(CH_2)_q-\overset{\overset{O}{\|}}{C}-OH \qquad IX$$

is first treated with an acid chloride of the formula $$R_{11}-\overset{\overset{O}{\|}}{C}-Cl \qquad X$$

in the presence of a base, such as sodium hydroxide, in a solvent mixture such as water and tetrahydrofuran to give an acid of the formula $$R_{11}-\overset{\overset{O}{\|}}{C}-NH-(CH_2)_m-A-(CH_2)_q-\overset{\overset{O}{\|}}{C}-OH. \qquad XI$$

The acid of formula XI is treated with isobutylchloroformate in the presence of a base, such as triethylamine, in a solvent, such as tetrahydrofuran, to form an intermediate mixed anhydride which is directly treated with diazomethane to form an intermediate diazoketone of the formula $$R_{11}-\overset{\overset{O}{\|}}{C}-NH-(CH_2)_m-A-(CH_2)_q-\overset{\overset{O}{\|}}{C}-CHN_2. \qquad XII$$

The diazoketone XII is reacted with anhydrous hydrogen chloride to form a chloromethyl ketone of the formula $$R_{11}-\overset{\overset{O}{\|}}{C}-NH-(CH_2)_m-A-(CH_2)_q-\overset{\overset{O}{\|}}{C}-CH_2-Cl. \qquad XIII$$

The compound of formula XIII is coupled with a diethylmalonate derivative having the formula $$\begin{array}{c} R_5 \;\; O \\ | \;\;\;\; \| \\ HC-C-OCH_2CH_3 \\ | \\ C=O \\ | \\ OCH_2CH_3 \end{array} \qquad XIV$$

in a solvent, e.g. tetrahydrofuran, and in the presence of a base, e.g. sodium hydride, to provide a compound of the formula $$R_{11}-\overset{\overset{O}{\|}}{C}-NH-(CH_2)_m-A-(CH_2)_q-\overset{\overset{O}{\|}}{C}-CH_2-\overset{\overset{R_5}{|}}{\underset{\underset{OCH_2CH_3}{|}}{\underset{C=O}{|}}{C}}-\overset{\overset{O}{\|}}{C}-OCH_2CH_3. \qquad XV$$

Compound XV in a solvent, e.g. aqueous ethanol, is treated in a strong base, such as sodium hydroxide, and thereafter with hydrochloric acid and heat to provide the compounds of formula III where Y is —CH$_2$— and X is $$R_{11}-\overset{\overset{O}{\|}}{C}-NH-(CH_2)_m-A-(CH_2)_q-\overset{\overset{O}{\|}}{C}-.$$

Reaction with compound II, as above, provides the corresponding compounds of formula I.

To make compounds of formula I wherein Y is —CH$_2$—, X is $$R_6-(CH_2)_m-A-(CH_2)_q-\overset{\overset{}{N}}{\underset{R_{10}}{|}}-\overset{\overset{O}{\|}}{C}-$$

for which $R_6$ is $$R_{11}-\overset{\overset{O}{\|}}{C}-NH-$$

and $R_5$ is —(CH$_2$)$_n$-aryl and n=1, a compound of the formula $$\begin{array}{c} Ar \\ | \\ CH \;\; O \\ \| \;\;\; \| \\ C-C-OCH_2CH_3 \\ | \\ CH_2-C-OH \\ \| \\ O \end{array} \qquad XVI$$

(the preparation of which has been described in J. Amer. Chem. Soc., 90, 3495, (1968)), is hydrogenated in the presence of a palladium on carbon catalyst to provide a compound having the formula $$\begin{array}{c} R_5 \;\; O \\ | \;\;\;\; \| \\ CH-C-OCH_2CH_3 \\ | \\ CH_2-C-OH \\ \| \\ O \end{array} \qquad XVII$$

Compound XVII is reacted with a compound of the formula $$R_{11}-\overset{\overset{O}{\|}}{C}-NH-(CH_2)_m-A-(CH_2)_q-\overset{\overset{}{N}H}{\underset{R_{10}}{|}} \qquad XVIII$$

in the presence of a catalyst, such as hydroxybenzotriazole, and dicyclohexylcarbodiimide to provide the ethyl ester of the formula

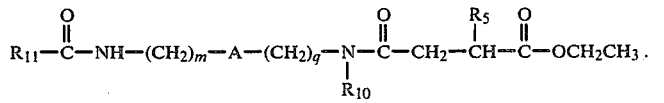   XIX

To prepare an amine of formula XVIII, an alcohol of the formula

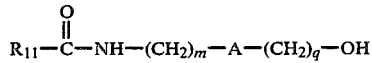   XX is treated with p-toluenesulfonyl chloride in the presence of a base such as pyridine to form a tosylate of the formula

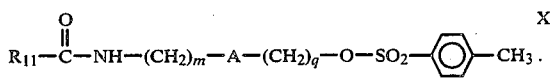   XXI

The compound of formula XXI is alkylated with an amine of the formula $R_{10}$—$NH_2$   XXII to provide the amine of formula XVIII.

Compound XIX, in a solvent such as aqueous ethanol, is treated with a strong base, e.g. sodium hydroxide to provide the compounds of formula III wherein Y is —$CH_2$— and X is

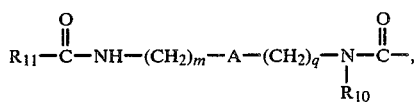

and $R_5$ is —$(CH_2)_n$-aryl and n=1. Reaction with compound II, as above, provides the corresponding compounds of formula I.

Alternatively, to make the compounds of formula I where Y is —$CH_2$— and X is

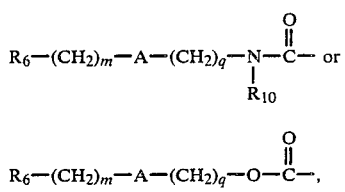

for which $R_6$ is

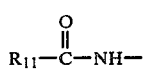

and $R_5$ is —$(CH_2)_n$-aryl and n=1 to 5, a dialkylmalonate of the formula

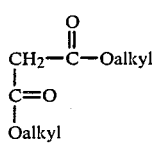   XXIII in a solvent, such as tetrahydrofuran, is treated with sodium hydride and thereafter reacted with a compound of the formula $R_5$—Cl or $R_5$—Br   XXIV to provide a compound having the formula

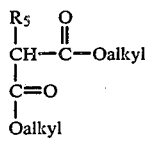   XXV

Compound XXV, in a solvent such as aqueous ethanol, is treated with a strong base, e.g. sodium hydroxide, and thereafter with hydrochloric acid to provide

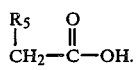   XXVI

Compound XXVI is treated with benzyl alcohol and 4-dimethylamino pyridine in a solvent, e.g. methylene chloride, in the presence of dicyclohexylcarbodiimide to provide the ester of the formula

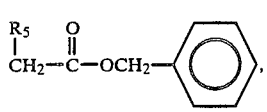   XXVII which is treated with diisopropylamine and n-butyl lithium in a solvent such as tetrahydrofuran, and thereafter reacted with t-butyl bromoacetate to provide

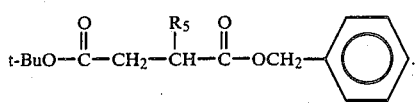   XXVIII

Compound XXVIII, in a solvent, such as methylene chloride, is treated with a strong acid, e.g. trifluoroacetic acid, to provide a compound of the formula

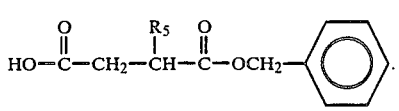   XXIX

Compound XXIX, in a solvent, such as tetrahydrofuran, is coupled with the amine of formula XVIII or the alcohol of formula XX in the presence of a catalyst, such as hydroxybenzotriazole or dimethylaminopyridine, and dicyclohexylcarbodiimide to provide the compounds of formula III where Y is —$CH_2$— and X is

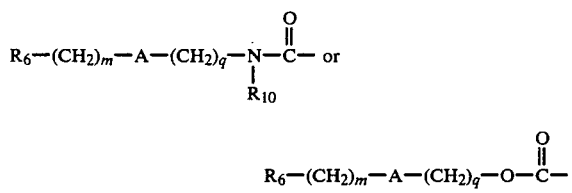

for which $R_6$ is

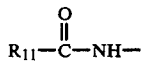

and $R_5$ is —$(CH_2)_n$-aryl and $n=1$ to 5. Reaction with compound II, as above, provides the corresponding compounds of formula I.

To make the compounds of formula I where Y is —$CH_2$— and X is $R_6$—$(CH_2)_m$—$(CH_2)_q$—A—S— and where $R_6$ is

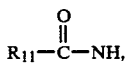

a compound of the formula

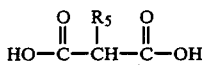   XXX is reacted with dimethylamine in the presence of formaldehyde to provide a compound of the formula

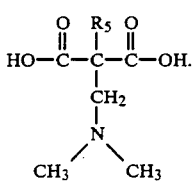   XXXI

Compound XXXI is heated to provide the acrylic acid of the formula

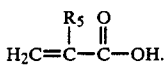   XXXII

Compound XXXII, in a solvent such as piperidine, is reacted with a compound of the formula

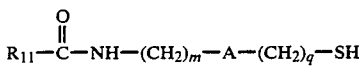   XXXIII to provide

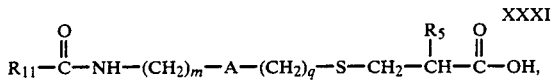   XXXIV that is, the compounds of formula III wherein Y is —$CH_2$— and X is $R_6$—$(CH_2)_m$—A—$(CH_2)_q$—S— and $R_6$ is

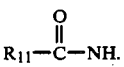

Reaction with compound II, as above, provides the corresponding compounds of formula I.

In the above reaction, compound XXXIII is prepared by treating the tosylate of formula XXI with mercaptoacetic acid to provide the thioester of formula

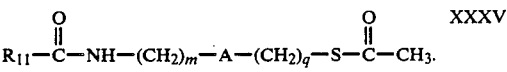   XXXV

The thioester of formula XXXV is hydrolyzed with aqueous ammonium hydroxide to yield the desired compound of formula XXXIII.

Alternatively, a compound of the formula XXXII may be esterified by reaction with ethanol in the presence of dicyclohexylcarbodiimide and a catalyst such as dimethylaminopyridine to give a compound of the formula

   XXXIIa

Compound XXXIIa, in a solvent such as ethanol is then reacted with a compound of the formula XXXIII in the presence of a base such as sodium ethoxide to give a compound of the formula

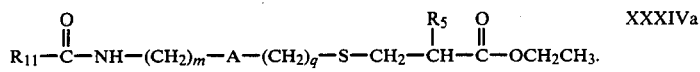   XXXIVa

Compound XXXIVa is treated with sodium hydroxide to give compound XXXIV. Compound XXXIV can thereafter be converted to the corresponding compounds of formula I as described above.

When X is $R_6$—$(CH_2)_m$—A—$(CH_2)_q$—SO—, compound XXXIV in a solvent, e.g. methanol, is treated with hydrogen peroxide. When X is $R_6$—$(CH_2)_m$—A—$(CH_2)_q$—$SO_2$—, compound XXXIV, in a solvent such as methanol, is treated with potassium monopersulfate. The resulting species of formula III can be reacted with compound II, as above, to provide the compounds of formula I wherein Y is —$CH_2$— and X is $R_6$—$(CH_2)_m$—A—$(CH_2)_q$—SO— and $R_6$—$(CH_2)_m$—A—$(CH_2)_q$—$SO_2$—, respectively.

To make compounds of formula I where Y is —$CH_2$— and X is

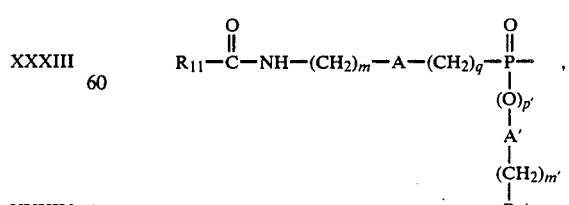

a compound of the formula

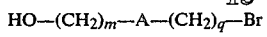 XXXVI is treated with t-butyldimethylsilylchloride and imidazole in a solvent, such as dichloromethane, to provide the protected alcohol of the formula

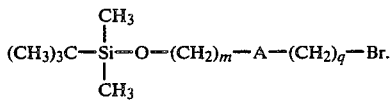 XXXVII

The compound of formula XXXVII is converted to its corresponding Grignard reagent by reaction with magnesium in a solvent, such as diethyl ether or tetrahydrofuran, followed by treatment with dimethychlorophosphite to provide

XXXVIII

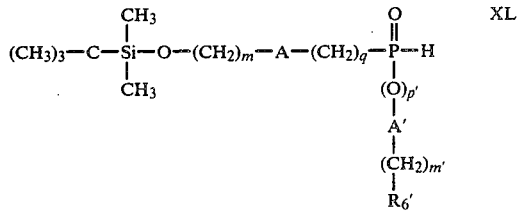 XL which is reacted with the acrylic acid of formula XXXII in dichloromethane in the presence of bis(trimethylsilyl)trifluoroacetamide to provide a compound of formula

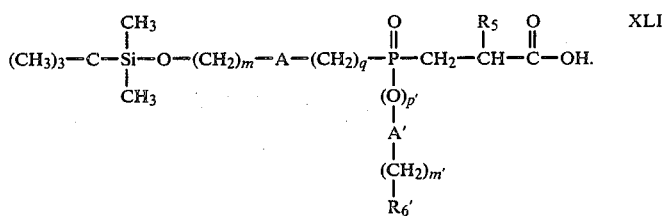 XLI

The compound of formula XLI is esterified with t-butanol using dicyclohexylcarbodiimide and dimethylaminopyridine in dichloromethane to provide the ester of the formula

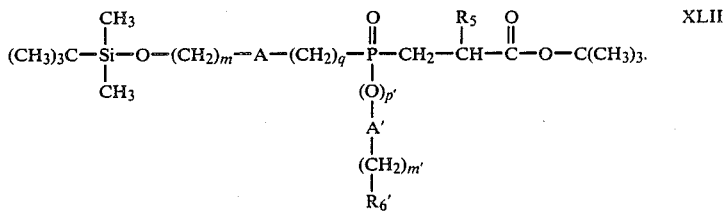 XLII

The compound of formula XLII is treated with aqueous hydrofluoric acid and acetonitrile to provide the corresponding alcohol which is converted to the tosylate of the formula

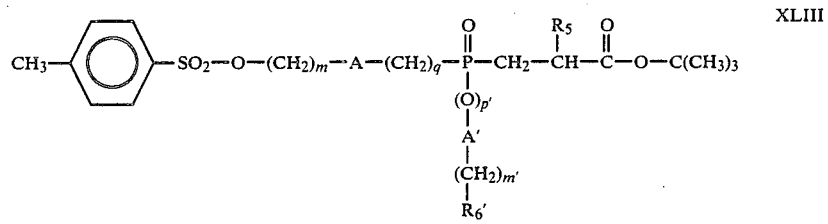 XLIII by treatment with p-toluenesulfonyl chloride and pyridine. The tosylate of formula XLIII is treated with methanolic ammonia to provide an amine of the formula The compound of formula XXXVIII is hydrolyzed with aqueous sodium hydroxide, then coupled to an alcohol of formula

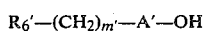 XXXIX to give the compound of formula

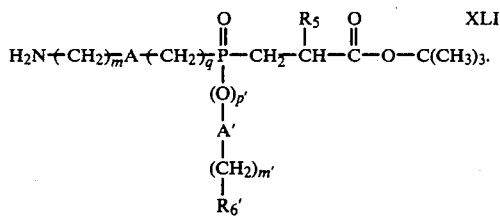

The amine of formula XLIV is acylated using an acid chloride of the formula

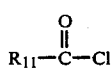

in the presence of a base, such as triethylamine, in a solvent, such as dichloromethane, to give an ester of the formula

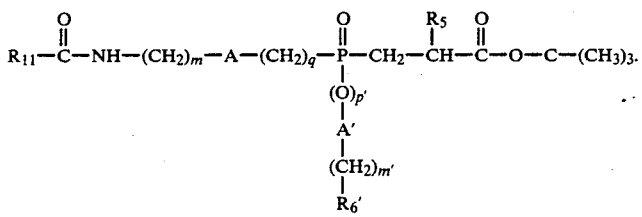

The ester of formula XLVI is hydrolyzed with anhydrous hydrochloric acid in dioxane to produce the acid of the formula

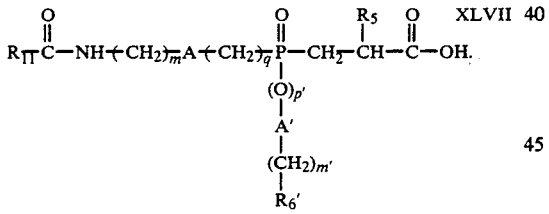

The acid of formula XLVII is coupled to compound II using a reagent, such as dicyclohexylcarbodiimide, in the presence of hydroxybenzotriazole in a solvent, such as dimethylformamide, to provide the corresponding compound of formula I.

To make compounds of formula I where Y is —CH$_2$— and X is

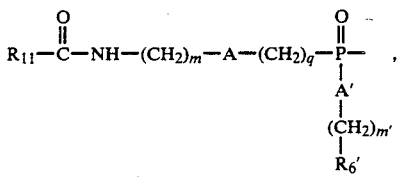

the compound of the formula XXXVIII is treated with a Grignard reagent of the formula

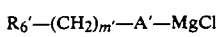

to provide the compound of formula

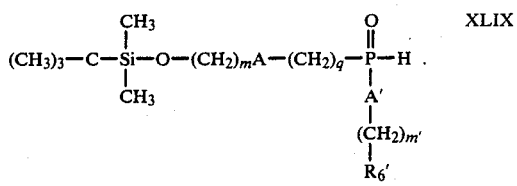

The compound of formula XLIX is converted to the corresponding compound of formula I in the manner described above for the compound of formula XL.

To make compounds of formula I where Y is —CH$_2$— and X is

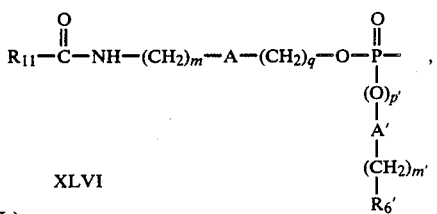

the alcohol of formula XX is reacted with phosphorus trichloride in the presence of a base, such as triethylamine, to provide, after hydrolytic workup, the compound of the formula

which is coupled to an alcohol of formula XXXIX using dicylcohexylcarbodiimide and dimethylaminopyridine to provide the compound of the formula

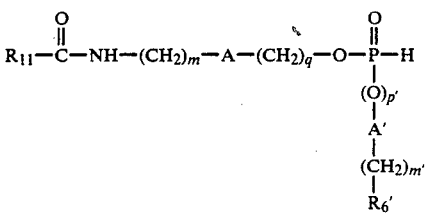

which is reacted with the acrylic acid of formula XXXII in dichloromethane in the presence of bis(trimethylsilyl)trifluoroacetamide to provide an acid of the formula

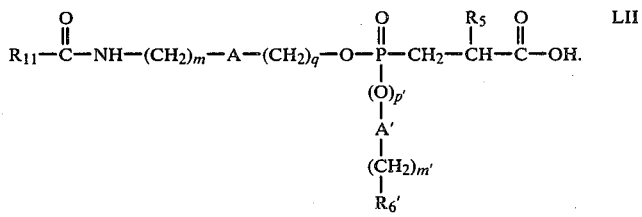 LII

The acid of formula LII is converted to the corresponding compound of formula I in the manner described above for the compounds of formula III.

To make compounds of formula I where Y is —CH₂— and X is

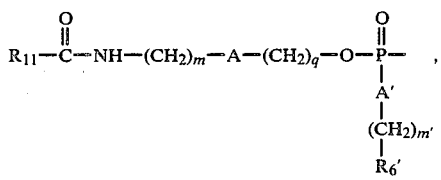

the Grignard reagent of formula XLVIII is reacted with dimethyl chlorophosphite in a solvent, such as diethyl ether, followed by treatment with acid to form a compound of the formula

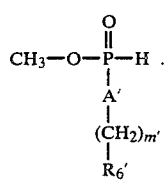 LIII

The compound of formula LIII is hydrolyzed with aqueous sodium hydroxide, then coupled to an alcohol of formula XX using dicyclohexylcarbodiimide and dimethylaminopyridine to provide the compound of the formula

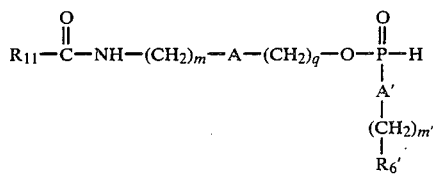 LIV which is converted to the corresponding compound of formula I in the manner described above for the compound of formula LI.

To make a compound of formula I wherein Y is —CH₂—, X is

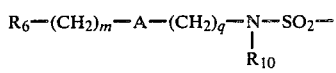

for which $R_6$ is

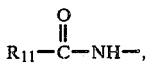, a compound of the formula

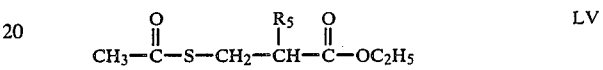 LV is prepared by treating the ester of formula XXXIIa with mercaptoacetic acid. The compound of formula LV is then treated with ammonium hydroxide solution to give a compound of the formula

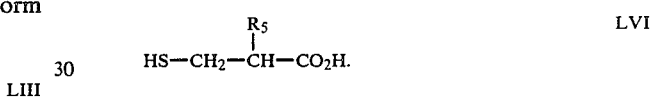 LVI

The compound of formula LVI is esterified, for example, by treatment with ethanol and dicyclohexylcarbodiimide in the presence of a catalyst, such as dimethylaminopyridine, to give a compound of formula

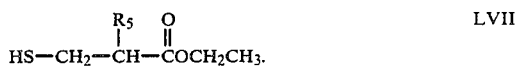 LVII

The compound LVII is treated with chlorine gas in a solvent such as aqueous acetic acid, to give the compound

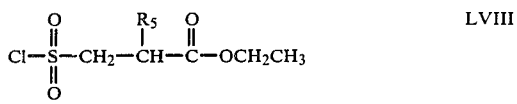 LVIII which is reacted with the amine of formula XVIII to give a compound of the formula

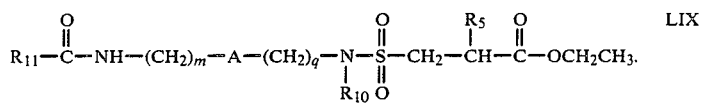 LIX

Compound LIX is saponified with a strong base, such as sodium hydroxide, to give a compound of the formula

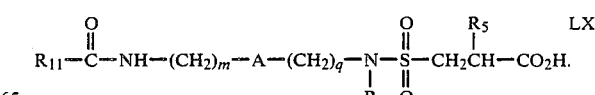 LX

Reaction of compound LX with compound II, as above, provides the corresponding compounds of formula I.

To make a compound of formula I wherein Y is —CH$_2$—, X is R$_6$—(CH$_2$)$_m$—A—(CH$_2$)$_q$— for which R$_6$ is

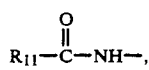

a ketone of formula XV, wherein X is R$_6$—(CH$_2$)$_m$—A—(CH$_2$)$_{q-1}$—, is treated with ethanedithiol in the presence of an acid, such as boron trifluoride etherate complex, to provide the thioketal of formula

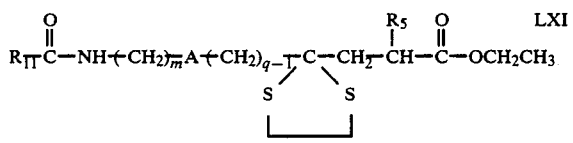

which is desulfurized by treatment with activated Raney nickel to provide the compound of formula

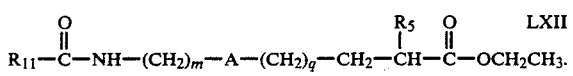

Compound LXII in a solvent, e.g. aqueous ethanol, is treated with a strong base, such as sodium hydroxide, and thereafter with hydrochloric acid and heat to provide the compounds of formula III where Y is —CH$_2$— and X is R$_6$—(CH$_2$)$_m$—A—(CH$_2$)$_q$— for which R$_6$ is

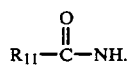

Reaction with compound II, as above, provides the corresponding compounds of formula I.

To prepare compounds of formula I in which Y is —NH—, the amine of formula II is coupled to a protected amino acid of the formula

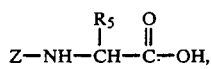

for which Z can be either t-butoxycarbonyl or benzyloxycarbonyl, using dicyclohexylcarbodiimide in the presence of hydroxybenzotriazole in a solvent, such as dimethylformamide, to afford a compound of the formula

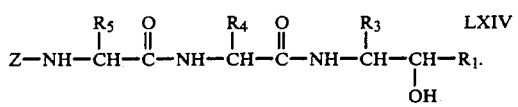

The protecting group Z is removed from the compound of formula LXIV by hydrogenolysis using palladium hydroxide on carbon in the presence of hydrogen gas in a solvent, such as methanol, when Z is benzyloxycarbonyl, or by treatment with anhydrous hydrogen chloride in dioxane when Z is t-butoxycarbonyl, to provide the amine (or corresponding HCl salt thereof) of the formula

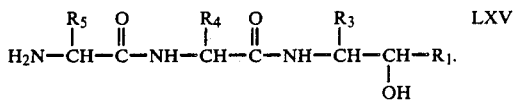

To make a compound of formula I wherein Y is —NH—, X is

for which R$_6$ is

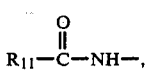

the acid of formula XI is coupled to the amine of formula LXV to provide the corresponding compound of formula I.

To make a compound of formula I wherein Y is —NH—, X is

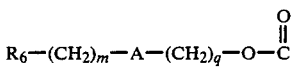

for which R$_6$ is

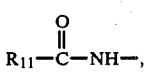

the amine of formula LXV is treated with p-nitrophenylchloroformate to form the p-nitrophenyl carbamate of formula

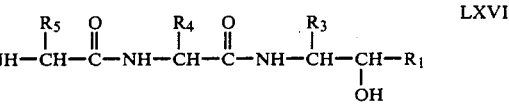

which is next reacted with the alcohol of formula XX in the presence of a base, such as n-methylmorpholine, and a catalyst, such as dimethylaminopyridine, in a solvent, such as dimethylformamide, to provide the corresponding compound of formula I.

To make a compound of formula I wherein Y is —NH—, X is

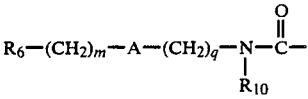

for which R$_6$ is

the compound of formula LXVI is treated with the amine of formula XVIII to form the corresponding compound of formula I.

To make a compound of formula I wherein Y is —NH—, X is $R_6$—$(CH_2)_m$—A—$(CH_2)_q$— for which $R_6$ is

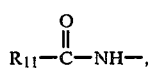

the alcohol of formula XX wherein X is

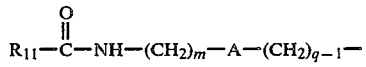

is oxidized to an aldehyde of the formula

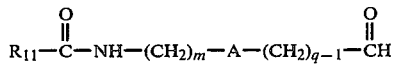 LXVII which is subsequently coupled to the amine of formula LXV by reductive alkylation performed by reacting the aldehyde and amine together in a solvent such as methanol in the presence of hydrogen gas and palladium hydroxide on carbon catalyst, or by mixing the amine and aldehyde in a solvent such as pH 8 buffered aqueous ethanol and adding the reagent, sodium cyanoborohydride, to form the corresponding compound of formula I.

To make a compound of formula I wherein Y is —NH—, X is $R_6$—$(CH_2)_m$—A—$(CH_2)_q$—$SO_2$— for which $R_6$ is

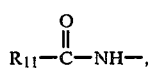

the compound of formula XXXIII is treated with chlorine gas in a solvent such as aqueous acetic acid to give the compound of formula

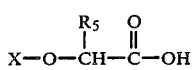 LXVIII which is reacted with the amine of formula LXV in the presence of a base, such as diisopropylethylamine, in a solvent, such as dimethylformamide, to provide the corresponding compound of formula I.

The compounds of formula I wherein Y is —O— are prepared by coupling an amine of the formula $$H_2N-\underset{R_4}{\overset{}{CH}}-\overset{O}{\overset{\|}{C}}-NH-\underset{R_3}{\overset{}{CH}}-\underset{OH}{\overset{}{CH}}-R_1 \quad \text{II}$$

(prepared as described above for either compound II or compound LXII) with the compound of the formula $$X-O-\underset{R_5}{\overset{}{CH}}-\overset{O}{\overset{\|}{C}}-OH \quad \text{LXIX}$$

in a solvent, e.g. dimethylformamide, and in the presence of one or more coupling agents, e.g. dicyclohexylcarbodiimide and/or hydroxybenzotriazole hydrate.

To make the compounds of formula I wherein Y is —O— and X is

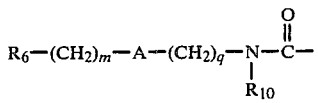

and $R_6$ is

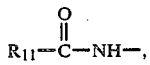

a compound of the formula

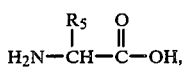 LXX in sulfuric acid, is treated with sodium nitrite in water to provide a compound having the formula

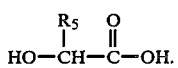 LXXI

Compound LVI, in an organic solvent, such as dimethylformamide, and in the presence of a base, such as sodium bicarbonate, is treated with a compound of the formula Br-Prot    LXXII (wherein "Prot" is an oxygen protecting group such as benzyl) to provide a compound of the formula

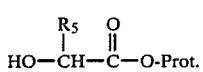 LXXIII

Compound LXXIII, in N-methyl morpholine and methylene chloride, is thereafter reacted with an aryl chloroformate, e.g.

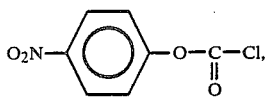 LXXIV in a solvent, such as methylene chloride, to yield a compound of the formula

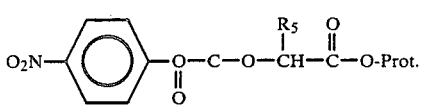 LXXV

Compound LXXV, in a solvent, such as toluene, can be reacted with a compound of formula XVIII to provide an intermediate of the formula

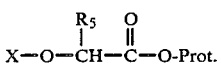 LXXVI

Reduction of compound LXXVI, for example by hydrogenation in ethyl acetate in the presence of a palladium/carbon catalyst, provides the compounds of formula LXIX. Reaction with an amine of formula II (or a protected form thereof), as described above, provides the compounds of formula I wherein Y is —O— and X is $$R_6-(CH_2)_m-A-(CH_2)_q-\underset{\underset{R_{10}}{|}}{N}-\overset{\overset{O}{\|}}{C}-$$

and $R_6$ is $$R_{11}-\overset{\overset{O}{\|}}{C}-NH.$$

To prepare the compounds of formula I wherein Y is —O— and X is $$R_6-(CH_2)_m-A-(CH_2)_q-\overset{\overset{O}{\|}}{C}-,$$

an intermediate of formula LV in a solvent, such as methylene chloride, is reacted with a carboxylic acid of formula XI.

This is carried out in the presence of dimethylaminopyridine and dicyclohexylcarbodiimide and provides a compound of formula LXXVI where Y is —O— and X is $$R_6-(CH_2)_m-A-(CH_2)_q-\overset{\overset{O}{\|}}{C}-.$$

This so-formed intermediate is thereafter reduced to provide a corresponding compound of formula LXIX and reacted with the amine of formula II, as above, to provide the compounds of formula I wherein Y is —O— and X is $$R_6-(CH_2)_m-A-(CH_2)_q-\overset{\overset{O}{\|}}{C}-.$$

To prepare the compounds of formula I wherein Y is —O— and X is $$R_6-(CH_2)_m-A-(CH_2)_q-O-\overset{\overset{O}{\|}}{C}-,$$

a compound of formula LXXIII is treated with p-nitrophenylchloroformate to form the p-nitrophenyl carbamate of formula $$NO_2-\!\!\bigcirc\!\!-O-\overset{\overset{O}{\|}}{C}-O-\underset{\underset{R_5}{|}}{CH}-\overset{\overset{O}{\|}}{C}-O\text{-Prot} \qquad \text{LXXVII}$$

which is next reacted with the alcohol of formula XX in the presence of a base, such as n-methylmorpholine, and a catalyst, such as dimethylaminopyridine, in a solvent, such as dimethylformamide, to provide the compound of the formula $$R_{11}-\overset{\overset{O}{\|}}{C}-NH-(CH_2)_m-A-(CH_2)_q-O-\overset{\overset{O}{\|}}{C}-O-\underset{\underset{R_5}{|}}{CH}-\overset{\overset{O}{\|}}{C}-O\text{-Prot} \qquad \text{LXXVIII}$$

which is reduced to provide the corresponding compound of formula LXIX which is coupled with an amine of formula II, as described above, to provide the compounds of formula I wherein Y is —O— and X is $$R_{11}-\overset{\overset{O}{\|}}{C}-NH-(CH_2)_m-A-(CH_2)_q-O-\overset{\overset{O}{\|}}{C}-.$$

To prepare the compounds of formula I wherein Y is —O— and X is $R_6-(CH_2)_m-A-(CH_2)_q-$, the intermediate of formula LXXIII treated with the tosylate of formula XXI to provide the compound of the formula $$R_{11}-\overset{\overset{O}{\|}}{C}-NH-(CH_2)_m-A-(CH_2)_q-O-\underset{\underset{R_5}{|}}{CH}-\overset{\overset{O}{\|}}{C}-O\text{-Prot} \qquad \text{LXXIX}$$

which is converted to the corresponding compound of formula I in the manner described above for compound LXXVIII.

To make compounds of formula I where Y is —O— and X is $$R_{11}-\overset{\overset{O}{\|}}{C}-NH-(CH_2)_m-A-(CH_2)_q-\underset{\underset{\underset{\underset{R_6'}{|}}{(CH_2)_{m'}}}{\underset{|}{A'}}}{\overset{\overset{O}{\|}}{P}}- \quad ,$$

the compound of formula XXXVIII is reacted with the Grignard reagent of the formula XLVIII to provide a compound of formula $$(CH_3)_3-C-\underset{\underset{CH_3}{|}}{\overset{\overset{CH_3}{|}}{Si}}-O-(CH_2)_m-A-(CH_2)_q-\underset{\underset{\underset{\underset{R_6'}{|}}{(CH_2)_{m'}}}{\underset{|}{A'}}}{\overset{\overset{O}{\|}}{P}}-H \qquad \text{LXXX}$$

which is treated with phosphorous pentachloride in a solvent, such as methylene chloride, to provide the phosphinyl chloride of the formula $$(CH_3)_3-C-\underset{\underset{CH_3}{|}}{\overset{\overset{CH_3}{|}}{Si}}-O-(CH_2)_m-A-(CH_2)_q-\underset{\underset{\underset{\underset{R_6'}{|}}{(CH_2)_{m'}}}{\underset{|}{A'}}}{\overset{\overset{O}{\|}}{P}}-Cl \; . \qquad \text{LXXXI}$$

The compound of formula LXXXI is then coupled to the alcohol of formula LXXIII in a solvent, such as dichloromethane, using triethylamine and dimethylaminopyridine to give a compound of the formula

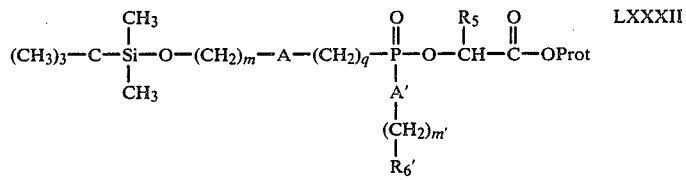  LXXXII which is reduced or saponified to the corresponding acid of the formula

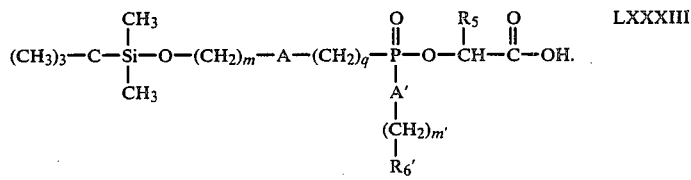  LXXXIII

The acid of formula LXXXIII can be converted to an acid of the formula

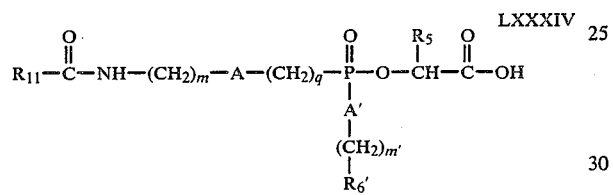  LXXXIV following the procedures described above for the conversion of the acids of formula XLI to acids of formula XLVII. The acid of formula LXXXIV can be converted to the corresponding compounds of formula I in the manner described above for compounds of formula XLVII.

To make compounds of formula I where Y is —O— and X is

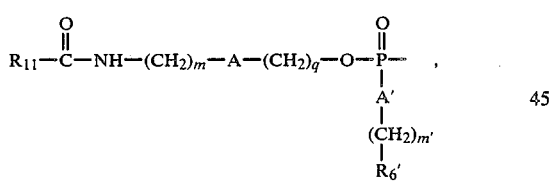

methanol is reacted with phosphorus trichloride in the presence of a base, such as triethylamine, followed by hydrolytic workup provides the compound of the formula

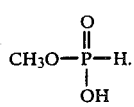  LXXXV

The compound of formula LXXXV is reacted with the alcohol of formula XX in a solvent, such as dichloromethane, and in the presence of dicyclohexylcarbodiimide and dimethylaminopyridine to give an ester of the formula

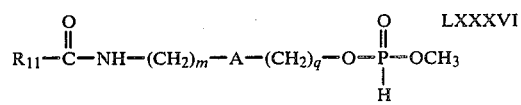  LXXXVI which is reacted with a Grignard reagent of formula XLVIII to provide a compound of the formula

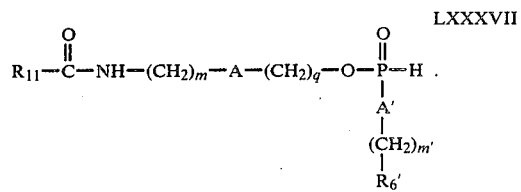  LXXXVII

The compound of formula LXXXVII is treated with thionylchloride to produce the phosphonyl chloride of the formula

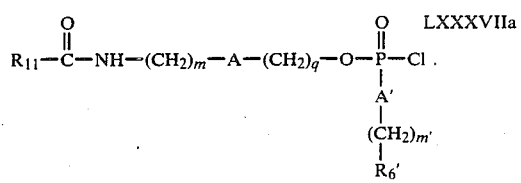  LXXXVIIa

The compound of formula LXXVIIa is coupled to the alcohol of formula LXXIII in a solvent, such as methylene chloride in the presence of triethylamine and dimethylaminopyridine, to provide a compound of the formula

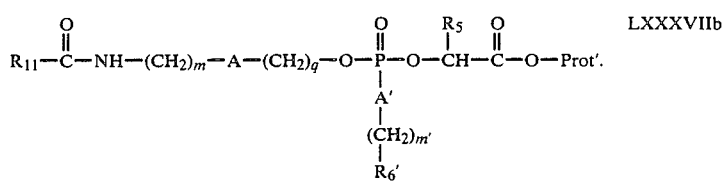  LXXXVIIb

After removal of the protecting group, Prot', by the deprotection means described above, the compound of formula LXXXVIIb is converted to the corresponding compounds of formula I in the manner described previously for compounds of formula LII.

To make compounds of formula I where Y is —O— and X is $$R_{11}-\overset{O}{\underset{\|}{C}}-NH-(CH_2)_m-A-(CH_2)_q-\overset{O}{\underset{\|}{\underset{|}{P}}}- ,$$
$$(O)_{p'}$$
$$|$$
$$A'$$
$$|$$
$$(CH_2)_{m'}$$
$$|$$
$$R_{6'}$$

the compound of formula LXXXV is reacted with an alcohol of the formula $$HO-A'-(CH_2)_{m'}-R_{6'} \qquad \text{LXXXVIII}$$

in a solvent, such as dichloromethane, and in the presence of dicyclohexylcarbodiimide and dimethylaminopyridine to provide $$R_{6'}-(CH_2)_{m'}-A'-O-\overset{O}{\underset{\|}{\underset{|}{P}}}-OCH_3 \qquad \text{LXXXIX}$$
$$H$$

which is reacted with a Grignard reagent of the formula $$\overset{CH_3}{\underset{|}{(CH_3)_3-C-\underset{|}{Si}-O-(CH_2)_m-A-(CH_2)_q-Mg-Br,}} \qquad \text{XC}$$
$$CH_3$$

prepared from the compound of formula XXXVII as described above, to give the compound of the formula $$\overset{CH_3}{\underset{|}{(CH_3)_3-C-\underset{|}{Si}-O-(CH_2)_m-A-(CH_2)_q-\overset{O}{\underset{\|}{\underset{|}{P}}}-H}} \cdot \qquad \text{XCI}$$
$$CH_3 \qquad\qquad\qquad (O)_{p'}$$
$$|$$
$$A'$$
$$|$$
$$(CH_2)_{m'}$$
$$|$$
$$R_{6'}$$

The compound of formula XCI is converted to the corresponding compounds of formula I in the manner as described above for compounds of formula LXXX.

To prepare compounds of formula I with $R_6$ equal to $NH_2$, the compounds of formula I with $R_6$ as $$R_{11}-\overset{O}{\underset{\|}{C}}-NH-$$

are synthesized with $R_{11}$ equal to t-butoxy or benzyloxy so that in a final step the group $$R_{11}-\overset{O}{\underset{\|}{C}}-$$

is replaced by H. When $R_{11}$ is equal to t-butoxy, the compound of formula I is treated with anhydrous acid, such as hydrogen chloride dissolved in dioxane, to provide the hydrochloride salt form of the compound of formula I with $R_6$ equal to $NH_2$. When $R_{11}$ is equal to benzyloxy, the compound of formula I is treated with hydrogen in the presence of palladium hydroxide on carbon catalyst to provide the compound of formula I with $R_6$ equal to $NH_2$.

To prepare compounds of formula I with $R_6$ equal to $NR_{13}R_{14}$, the compounds of formula I with $R_6$ equal to $NH_2$ are treated with an aldehyde at pH 7-8 in the presence of sodium cyanoborohydride to produce the product from reductive alkylation of formula I in which $R_6$ is —$NHR_{13}$. To obtain a second substituent on nitrogen, the preceding product is subjected to the same conditions as above with the appropriate aldehyde to yield a compound of formula I wherein $R_6$ is —$NR_{14}R_{13}$.

To prepare compounds of formula I with $R_6$ equal to NH—C(=NH)—$NH_2$, the compounds of formula I with $R_6$ equal to $NH_2$ are guanylated in a final step with a reagent such as O-methylisourea sulfate.

To make a compound of formula I wherein Y is —$CH_2$— and X is $R_6$—$(CH_2)_m$—A—$(CH_2)_q$—CO— and where $R_6$ is $$R_{12}-O-\overset{O}{\underset{\|}{C}}- \quad \text{or} \quad \overset{R_{13}}{\underset{R_{14}}{\diagdown}}N-\overset{O}{\underset{\|}{C}}-,$$

a compound of the formula $$(CH_3)_3C-O-\overset{O}{\underset{\|}{C}}-(CH_2)_m-A-(CH_2)_q-\overset{O}{\underset{\|}{C}}-OCH_3 \qquad \text{XCII}$$

is prepared by treating a monoacid, monoester of the formula $$HO-\overset{O}{\underset{\|}{C}}-(CH_2)_m-A-(CH_2)_q-\overset{O}{\underset{\|}{C}}-OCH_3 \qquad \text{XCIII}$$

with t-butanol in the presence of dicyclohexylcarbodiimide and dimethylaminopyridine in a solvent, such as dichloromethane. The resulting diester of formula XCII is then saponified by treatment first with sodium hydroxide in aqueous methanol followed by acidification to provide a compound of the formula $$(CH_3)_3C-O-\overset{O}{\underset{\|}{C}}-(CH_2)_m-A-(CH_2)_q-\overset{O}{\underset{\|}{C}}-OH. \qquad \text{XCIV}$$

The acid of formula XCIV is treated with isobutylchloroformate in the presence of a base, such as triethylamine, in a solvent, such as tetrahydrofuran, to form an intermediate mixed anhydride which is directly treated with diazomethane to form an intermediate diazoketone of the formula

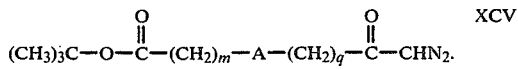

The diazoketone of formula XCV is reacted with anhydrous hydrogen chloride in a solvent, such as diethyl ether, to form a chloromethyl ketone of the formula

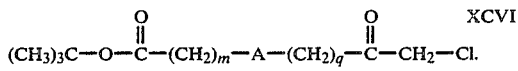

The compound of formula XCVI is coupled with a diethylmalonate derivative of formula XIV in a solvent, such as tetrahydrofuran, and in the presence of a base, such as sodium hydride, to provide a compound of the formula

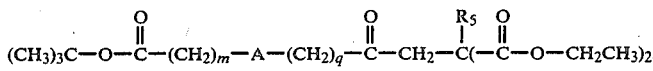

The compound of formula XCVII is then treated with sodium hydroxide in aqueous ethanol, then acidified and heated to decarboxylate to form an acid of the formula

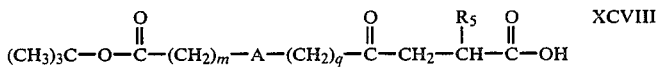

which is coupled to the amine of formula II to provide the compound of the formula

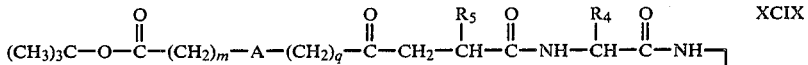

When the above compound of formula XCIX is treated with anhydrous acid, such as trifluoroacetic acid, the corresponding compound of formula I wherein $R_6$ is

is prepared.

Treatment of the compound of formula I wherein $R_6$ is

with an alcohol of the formula $$R_{12}-OH \qquad C$$

in the presence of dicyclohexylcarbodiimide and dimethylaminopyridine in a solvent, such as dichloromethane, provides the corresponding compounds of formula I with $R_6$ is

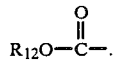

Treatment of the compound of formula I wherein $R_6$ is

with an amine of the formula

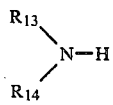

in the presence of dicyclohexylcarbodiimide and hydroxybenzotriazole in a solvent, such as dimethylformamide, provides the corresponding compounds of formula I wherein $R_6$ is

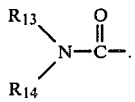

To make a compound of formula I wherein Y is —CH$_2$—, X is

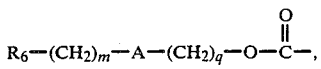

an alcohol of the formula

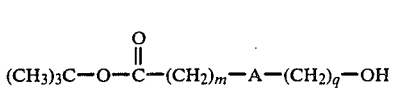

is coupled to an acid of formula XXIX using dicyclohexylcarbodiimide and dimethylaminopyridine, followed by reduction with hydrogen in the presence of palladium catalyst to remove the benzyl ester group providing an acid of the formula

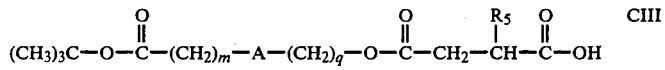

which is coupled an amine of formula II in the manner as described above for the compound XCVIII to provide the compound of formula

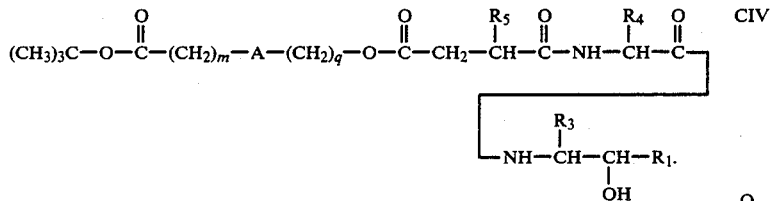

The compound of formula CIV is treated as described above for the compound XCIX to provide the corresponding compounds of formula I for which $R_6$ can be

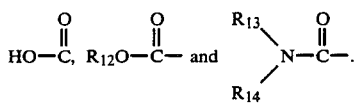

To make a compound of formula I wherein Y is —CH$_2$—, X is

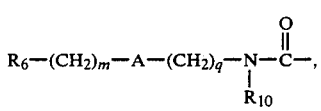

a compound of the formula CII is converted to the corresponding tosylate of the formula

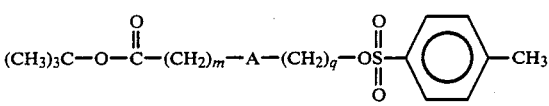

by treatment with p-toluenesulfonyl chloride in pyridine. The compound of formula CV is next reacted with an amine of formula XXII to provide a compound of the formula

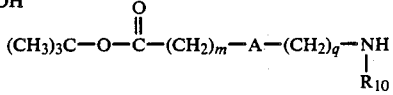

which is acylated with the acid of formula XXIX using dicyclohexylcarbodiimide and hydroxybenzotriazole in a solvent such as dimethylformamide, which, after removal of the benzyl ester group by saponification, provides the compound

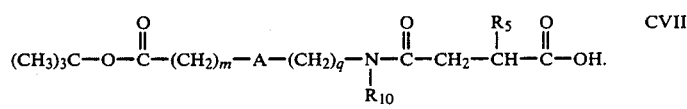

The compound of formula CVII is coupled an amine of formula II in the manner described above for the compound of XCVIII to provide the compound of the formula

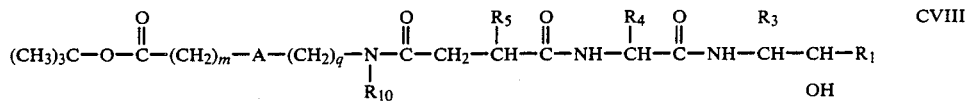

The compound of formula CVIII is treated as described above for the compound XCIX to provide the corresponding compounds of formula I for which $R_6$ can be

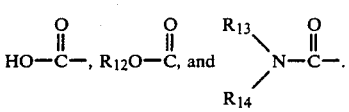

To make compounds of formula I wherein Y is —CH$_2$—, X is $R_6$—(CH$_2$)$_m$—A—(CH$_2$)$_q$—S—, $R_6$—(CH$_2$)$_m$—A—(CH$_2$)$_q$—SO and $R_6$—(CH$_2$)$_m$—A—(CH$_2$)$_q$—SO$_2$—, the tosylate of formula CV is converted to the acid of formula

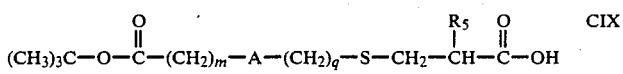

as described for the similar conversion of tosylate XXI to acid XXXIV. The acid CIX is coupled to the amine II to give

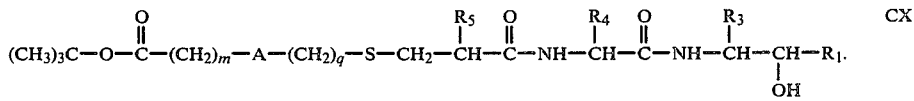

The compound of formula CX is treated as described above for the compound XCIX to provide the corresponding compounds of formula I for which $R_6$ can be

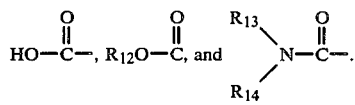

The preparation of analogous examples of compound I for which X is $R_6-(CH_2)_m-A-(CH_2)_q-SO-$ and $R_6-(CH_2)_m-A-(CH_2)_q-SO_2$ can be accomplished using the acid of formula CIX in the manner described for the acid of formula XXXIV, that is prior oxidation to the sulfoxide or sulfone intermediates prior to coupling to the amine of formula II. Subsequent conversion to compounds of formula I would proceed as described above.

To make compounds of formula I wherein Y is $-CH_2-$, X is

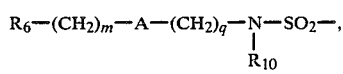

the earlier described compound of formula LVIII is treated with the amine of formula CVI in the presence of a base such as triethylamine and in a solvent, such as dimethylformamide, to provide

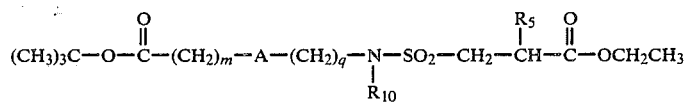

which is saponified with aqueous sodium hydroxide to provide, after acidification, the acid

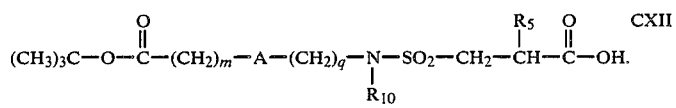

The acid of formula CXII is coupled to the amine of formula II to give

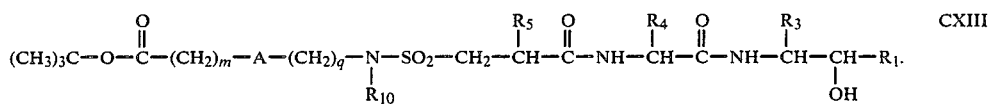

The compound of formula CXIII is treated as described above for the compound XCIX to provide the corresponding compounds of formula I for which $R_6$ can be

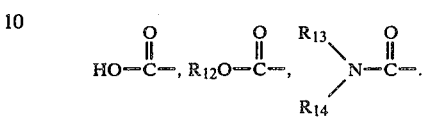

To make compounds of formula I wherein Y is $-CH_2-$, X is

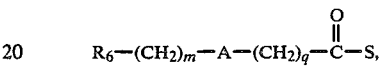

the previously described compound of formula XXXII is treated with mercaptoacetic acid to give

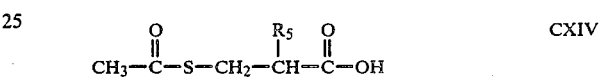

which is coupled to the amine of formula II to provide a compound of the formula

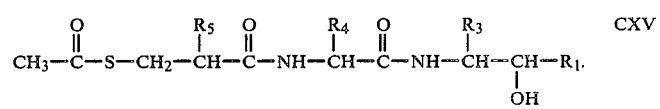

The compound of formula CXV is then treated with aqueous ammonium hydroxide in a solvent, such as methanol, or with mercuric trifluoroacetate in tetrahydrofuran followed by treatment with hydrogen sulfide gas, to provide the free sulfhydryl compound

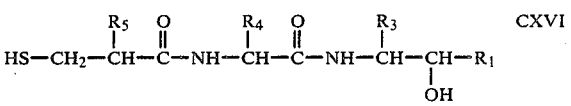

which is reacted with the acid of formula XCIV using dicyclohexylcarbodiimide and dimethylaminopyridine in a solvent, such as dichloromethane, to provide a compound of the formula

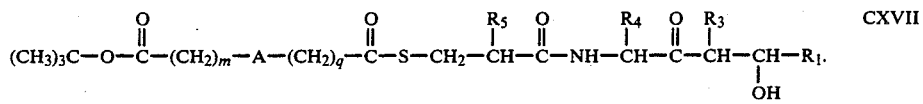
CXVII

The compound of formula CXVII is treated as described above for the compound XCIX to provide the corresponding compounds of formula I for which $R_6$ can be

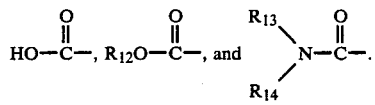

To make compounds of formula I wherein Y is $-CH_2-$ and X is

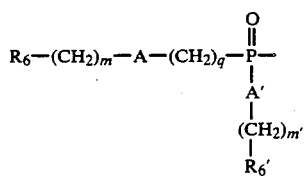

where $R_6$ is

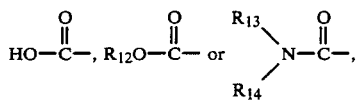

the tosylate of formula CV is treated with sodium bromide in acetone to provide a compound of the formula

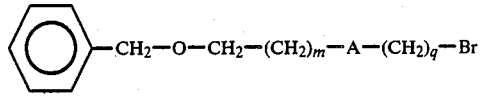
CXX which is converted to its corresponding Grignard reagent and reacted with dimethylchlorophosphite to provide

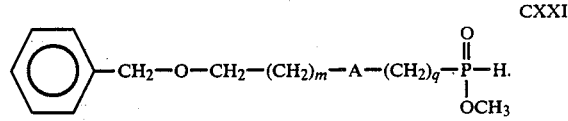
CXXI

The compound of formula CXXI is treated with a Grignard reagent of formula XLVIII to provide a compound of the formula

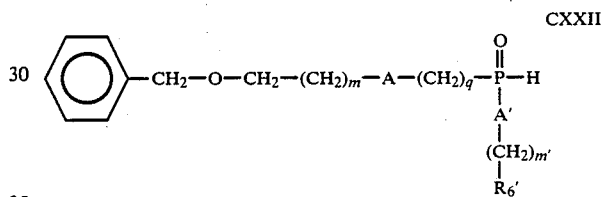
CXXII which is reacted with the acrylic acid of formula XXXII in dichloromethane in the presence of bis(trimethylsilyl)trifluoroacetamide to provide a compound of the formula

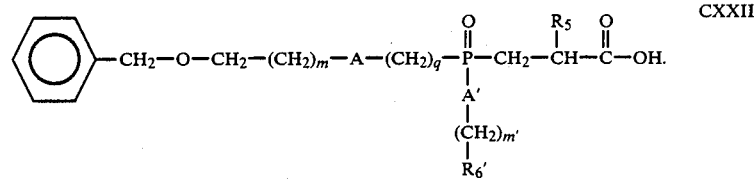
CXXII

The compound of formula CXXIII is esterified using methyl iodide and sodium bicarbonate in dimethylformamide, then reduced using hydrogen and a palladium catalyst to provide the alcohol of the formula

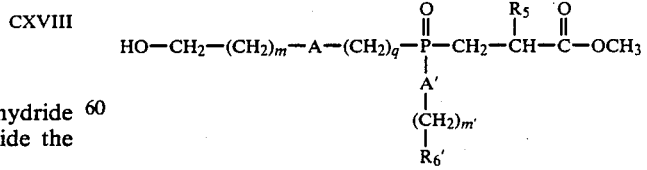
CXXIV

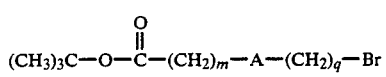
CXVIII which can be reduced with lithium aluminum hydride in a solvent, such as tetrahydrofuran, to provide the compound

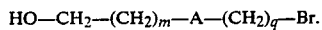 CXXIX

The alcohol CXIX can be treated with benzyl bromide and sodium hydride in tetrahydrofuran to afford the protected alcohol of the formula which is oxidized to a carboxylic acid using a reagent, such as ruthenium trichloride and sodium meta-periodate in a solvent mixture consisting of carbon tetrachloride, acetonitrile and water. The resulting acid is converted to the corresponding t-butyl ester using t-butanol and dicyclohexylcarbodiimide and dimethylaminopyridine to give a compound of formula

CXXV

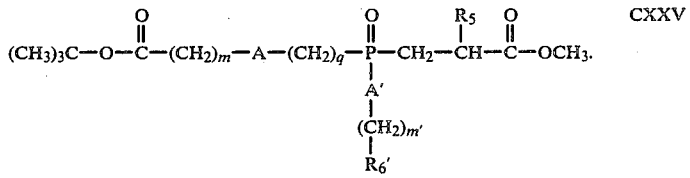

The compound of formula CXXV is saponified using aqueous sodium hydroxide followed by acidification to yield the corresponding acid which is coupled to the amine of formula II to provide

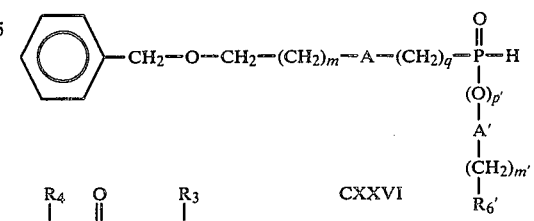

CXXVI

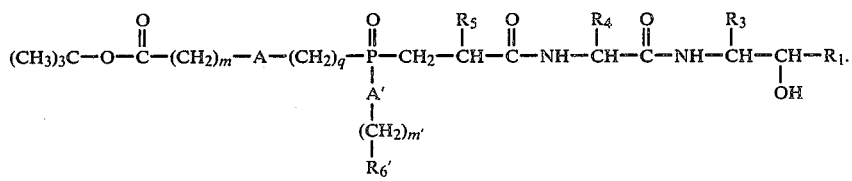

The compound of formula CXXVI is treated as described above for the compound XCIX to provide the corresponding compounds of formula I for which $R_6$ can be

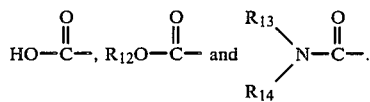

To make compounds of formula I wherein Y is —$CH_2$— and X is

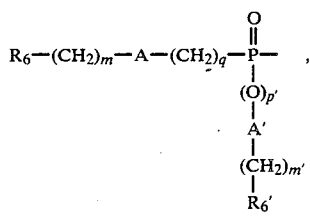

and p' is one and $R_6$ can be

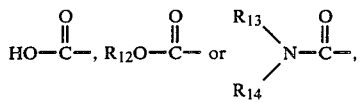

the compound of formula CXXI is hydrolyzed with aqueous sodium hydroxide, then coupled to an alcohol of formula XXXIX using dicyclohexylcarbodiimide and dimethylaminopyridine in a solvent, such as dichloromethane, to provide a compound of the formula

CXXVII which can be converted to the corresponding compounds of formula I in the manner described previously for compounds of formula CXXII.

To make compounds of formula I wherein Y is —$CH_2$— and X is

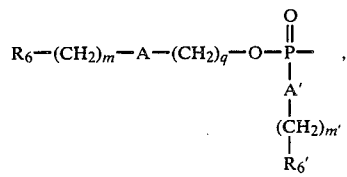

and $R_6$ can be

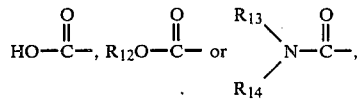

the compound of formula LIII is hydrolyzed with aqueous sodium hydroxide, then coupled to the alcohol of the formula

CXXVIII

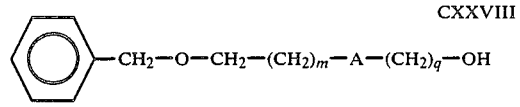

using dicyclohexylcarbodiimide and dimethylaminopyridine in a solvent, such as dichloromethane, to provide a compound of the formula

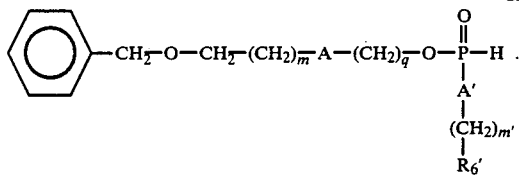

CXXIX

The alcohol of formula CXXVIII may be prepared by treating the alcohol of formula CII with acetic anhydride in pyridine to provide the compound of the formula

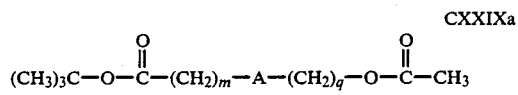

CXXIXa which is treated with trifluoroacetic acid to remove the t-butyl ester and the resulting acid group is selectively reduced using diborane to the alcohol of the formula

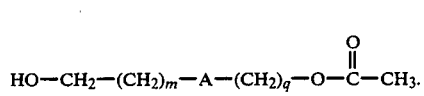

CXXIXb

The compound of formula CXXIXb is treated with benzyl bromide and sodium hydride in a solvent such as tetrahydrofuran, followed by subsequent reduction of the acetate ester group with a reagent, such as lithium aluminium hydride in tetrahydrofuran. Compounds of formula CXXIX can be converted to the corresponding compounds of formula I in the manner described previously for compounds of formula CXXII.

To make compounds of formula I wherein Y is —CH$_2$— and X is

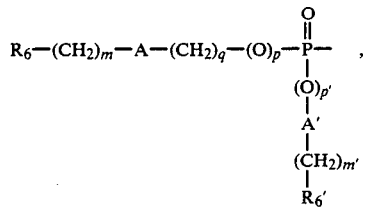

and p' is one and R$_6$ can be

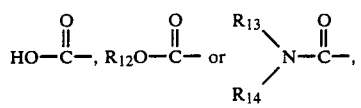

the alcohol of formula CXXVIII is reacted with phosphorous trichloride, in the presence of triethylamine to provide, after hydrolytic workup, a compound of the formula

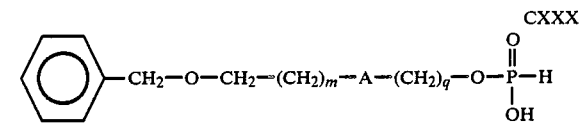

CXXX which is coupled to an alcohol of formula XXXIX using dicyclohexylcarbodiimide and dimethylaminopyridine in a solvent, such as dichloromethane, to provide a compound of the formula

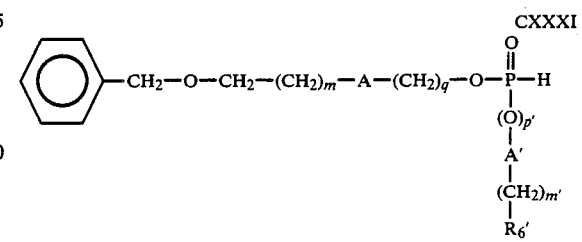

CXXXI which can be converted to the corresponding compounds of formula I in the manner described previously for compounds of formula CXXII.

To make a compound of formula I wherein Y is —NH— and X is

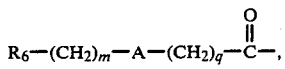

and R$_6$ can be

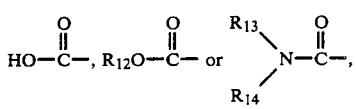

the acid of formula XCIV is coupled with the previously described amine of formula LXV using dicyclohexylcarbodiimide and hydroxybenzotriazole in a solvent such as dimethylformamide to provide the compound of the formula

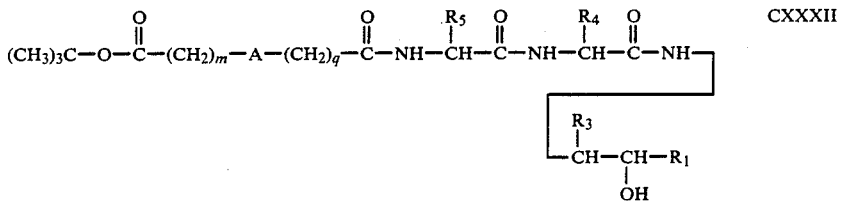

CXXXII which can be converted to the corresponding compounds of formula I as described for the compound of formula XCIX.

To make a compound of formula I wherein Y is —NH—, X is

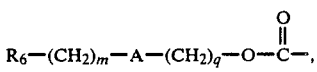

and R$_6$ can be the alcohol of formula CII is treated with p-nitro-

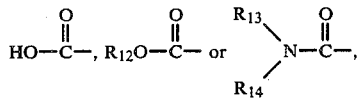

the amine of the formula CVI is treated with p-nitrophenylchloroformate to provide the compound of formula

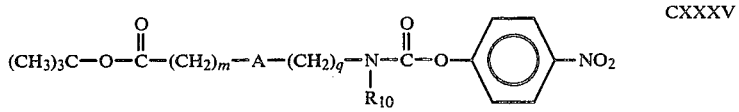 CXXXV which is acylated with the amine of formula LXV in a solvent, such as dimethylformamide, using a base, such as triethylamine, providing the compound of the formula

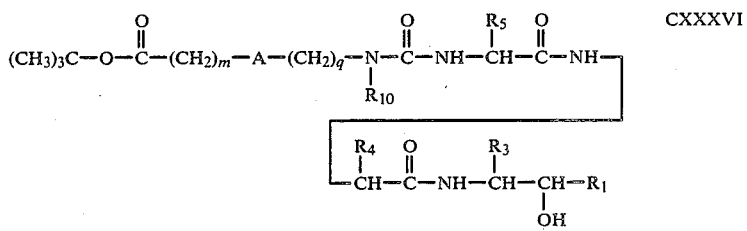 CXXXVI phenylchloroformate to provide the intermediate compound of the formula

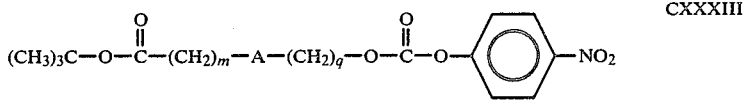 CXXXIII which is acylated with the amine of formula LXV in a solvent, such as dimethylformamide, using a base, such as triethylamine, providing the compound of the formula which can be converted to the corresponding compounds of formula I as described for the compound of formula XCIX.

To make compounds of formula I wherein Y is —NH—, X is $R_6$—$(CH_2)_m$—A—$(CH_2)_q$—$SO_2$—, and $R_6$ can be

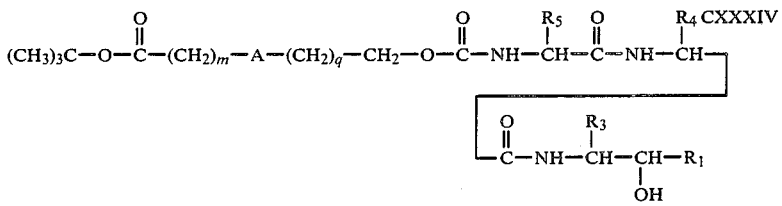 CXXXIV which can be converted to the corresponding compounds of formula I as described for the compound of formula XCIX.

To make a compound of formula I wherein Y is —NH—, X is

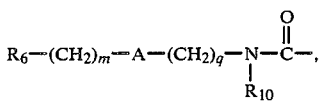

and $R_6$ can be

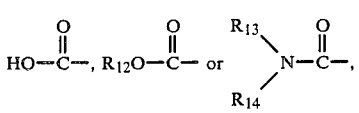

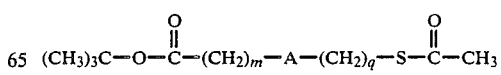

the tosylate of formula CV is treated with mercaptoacetic acid in the presence of a base, such as triethylamine, to form the compound of the formula (CH$_3$)$_3$C—O—C(=O)—(CH$_2$)$_m$—A—(CH$_2$)$_q$—S—C(=O)—CH$_3$  CXXXVII which is treated with aqueous ammonium hydroxide to yield the compound of the formula

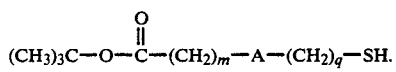

CXXXVIII

The compound of formula CXXXVIII is treated with chlorine gas in a solvent, such as aqueous acetic acid, to give the compound of the formula

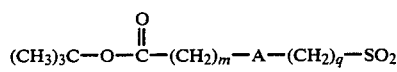

CXXXIX

Treatment of the amine LXV with compound CXXXIX in dimethylformamide in the presence of a base, such as triethylamine, provides the compound of the formula

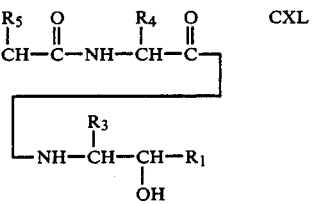

CXL which can be converted to the corresponding compounds of formula I as described for the compound of formula XCIX.

To make a compound of formula I wherein Y is —O— and X is

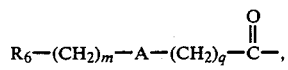

and $R_6$ can be

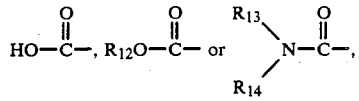

the alcohol of formula LXXIII is coupled with the previously described acid of formula XCIV using dicyclohexylcarbodiimide and dimethylaminopyridine in a solvent, such as dichloromethane, to provide a compound of the formula

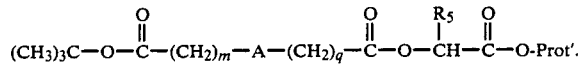

CXLI

When the protecting group (Prot') is benzyl, the compound of formula CXLI is reduced by treatment with hydrogen in the presence of a palladium catalyst in a solvent, such as methanol to provide the corresponding free acid which is coupled to an amine of formula II using dicyclohexylcarbodiimide and hydroxybenzotriazole in a solvent, such as dimethylformamide, to provide the compound of the formula

CXLII which can be converted to the corresponding compounds of formula I as described for the compound of formula XCIX.

To make a compound of formula I wherein Y is —O— and X is

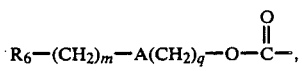

and $R_6$ can be

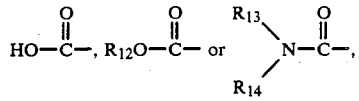

the previously described compound of formula LXXVII is treated with the alcohol of formula CII in a solvent, such as dimethylformamide using a base, such as triethylamine, and dimethylaminopyridine as a catalyst, to provide the compound

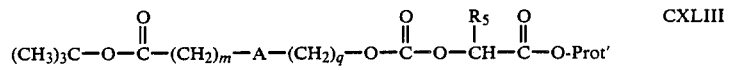

CXLIII which can be converted to the corresponding compounds of formula I as described for the compound of formula CXLI.

To make a compound of formula I wherein Y is —O— and X is

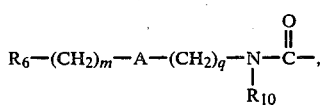

and R6 can be

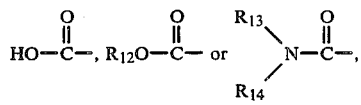

the amine of formula CVI is reacted with the compound of formula LXXVII to provide the compound

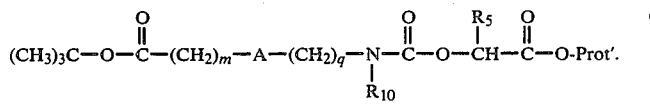

When the protecting group (Prot') is benzyl, the compound of formula CXLIV is reduced with hydrogen in the presence of palladium catalyst in a solvent such as methanol to provide the corresponding free acid, which is coupled to an amine of formula II using dicyclohexylcarbodiimide and hydroxybenzotriazole in a solvent, such as dimethylformamide, to provide the compound of the formula

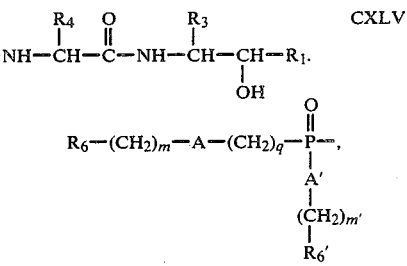

The compound of formula CXLV can be converted to the corresponding compounds of formula I in the manner described for compounds of the formula XCIX.

To make a compound of formula I wherein Y is —O— and X is R6—(CH2)m—A—(CH2)q—, and R6 can be

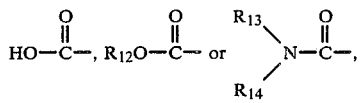

the alcohol of formula LXXIII is treated with sodium hydride in a solvent, such as tetrahydrofuran, to form an intermediate alkoxide which is directly reacted with the alkyl bromide of the formula CXX to provide the compound of the formula

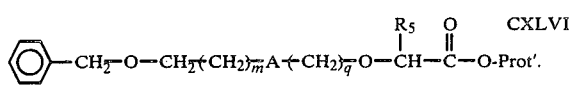

The benzyl group is reduced using hydrogen and palladium catalyst and the resulting alcohol is oxidized using ruthenium trichloride as described above to provide the acid of the formula

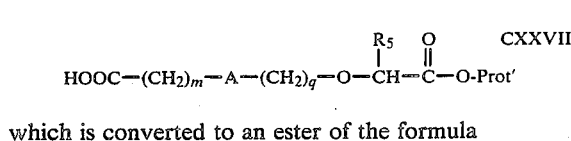

which is converted to an ester of the formula

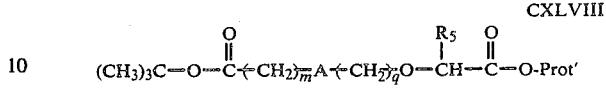

using t-butanol and dicyclohexylcarbodiimide in the presence of hydroxybenzotriazole.

the compound of formula CXLVIII can be converted to the corresponding compounds of formula I in the manner described for compounds of formula CXLIV, except that the protecting group, Prot', should be a methyl ester that is removed by saponification.

To make compounds of formula I where Y is —O— and X is $$R_6-(CH_2)_m-A-(CH_2)_q-\overset{O}{\underset{\underset{R_6'}{\underset{|}{(CH_2)_{m'}}}}{\underset{|}{\overset{\|}{P}}{-}}},$$

and R6 can be

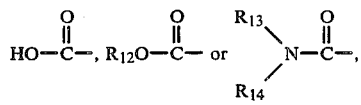

compounds of formula CXXII are treated with phosphorous pentachloride to provide the phosphinyl chloride of the formula $$\text{Ph}-CH_2-O-CH_2-(CH_2)_m-A-(CH_2)_q-\overset{O}{\underset{\underset{R_6'}{\underset{|}{(CH_2)_{m'}}}}{\underset{|}{\overset{\|}{P}}{-}}}-OH. \quad \text{CXLIX}$$

The compound of the formula CXLIX is then coupled to the alcohol of formula LXXIII in a solvent, such as dichloromethane, using dicyclohexylcarbodiimide and dimethylaminopyridine to give a compound of the formula

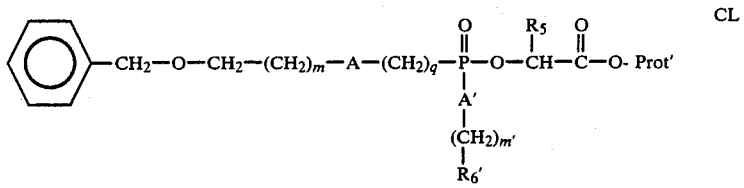
CL which is saponified to the corresponding acid

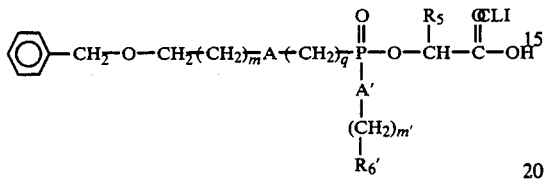
CLI

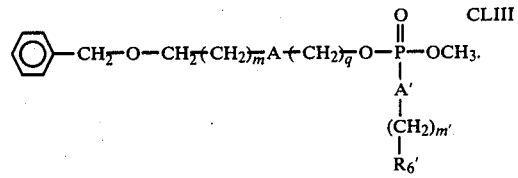
CLIII which can be converted to the corresponding compounds of formula I in the manner described above for compounds of the formula CXXIII.

To make compounds of formula I where Y is —O— and X is

The compound of formula CLIII is treated with thionyl chloride to provide an intermediate phosphonyl chloride which is coupled to an alcohol of formula LXXIII in a solvent such as methylene choride in the presence of triethylamine and dimethylaminopyridine to provide a compound of the formula

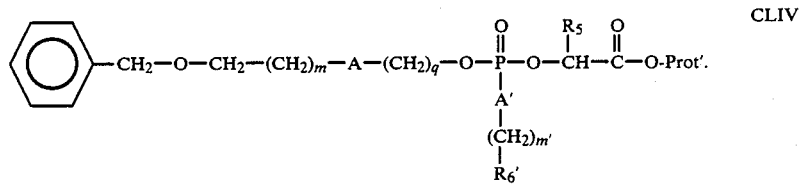
CLIV

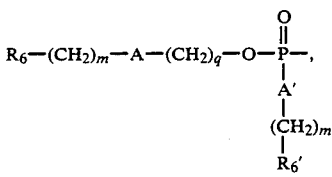

and R$_6$ is

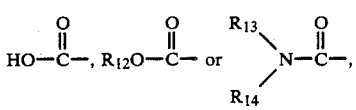

the compound of formula LXXXV is reacted with the alcohol of formula CXXVIII in a solvent, such as dichloromethane using dicyclohexylcarbodiimide and dimethylaminopyridine to form the compound of the formula

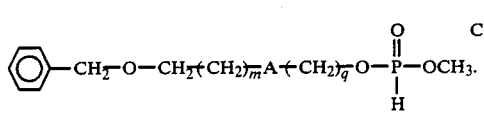
CLII

The compound of formula CLII is reacted with a Grignard reagent of formula XLVIII to provide a compound of the formula The compound of formula CLIV is converted to the corresponding compounds of formula I in the manner as described above for compounds of formula CL.

To make compounds of formula I where Y is —O— and X is

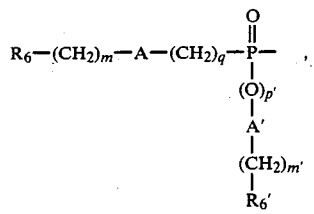

and R$_6$ is

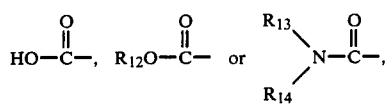

the compound of formula LXXXIX is reacted with the Grignard reagent derived from the previously described alkyl halide of formula CXX to give the compound of the formula

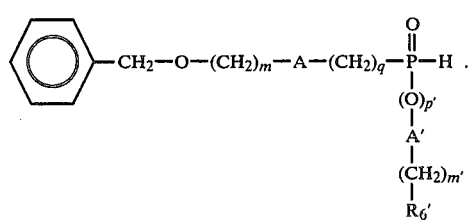 CLV

The compound of formula CLV is converted to the corresponding compounds of formula I in the manner as described above for compounds of formulula CLIV.

In the above reactions, if any of $R_3$, $R_4$ and $R_5$ are —$(CH_2)_n$-aryl wherein aryl is phenyl, 1-naphthyl, 2-naphthyl substituted with one or more hydroxy or amino groups, —$(CH_2)_n$-heterocyclo wherein heterocyclo is an imidazolyl, —$(CH_2)_n$—$NH_2$, —$(CH_2)_n$—SH, —$(CH_2)_n$—OH,

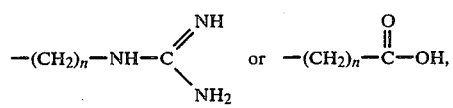

then the hydroxyl, amino, imidazolyl, mercaptan, carboxyl, or guanidinyl function should be protected during the reaction. Suitable protecting groups include benzyloxycarbonyl, t-butoxycarbonyl, benzyl, benzhydryl, trityl, tosyl, etc., and nitro in the case of guanidinyl. The protecting group is removed by hydrogenation, treatment with acid, or by other known means following completion of the reaction.

The various peptide intermediates employed in above procedures are known in the literature or can be readily prepared by known methods. See for example, the Peptides, Volume 1, "Major Methods of Peptide Bond Formation", Academic Press (1979).

Preferred compounds of this invention are those of formula I wherein

X—Y is

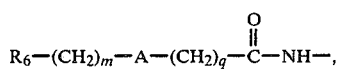
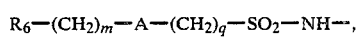
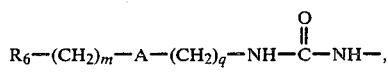
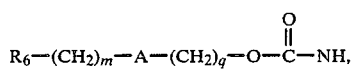
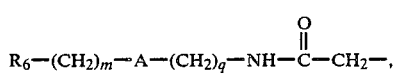
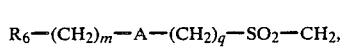
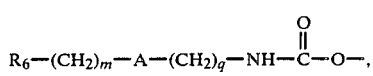

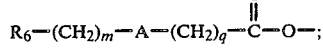

$R_3$ is straight or branched chain lower alkyl of 3 to 5 carbons, —$(CH_2)_n$-cyclopentyl, —$(CH_2)_n$-cyclohexyl, or

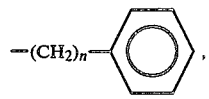

wherein n is an integer from 1 to 3;

$R_4$ is hydrogen, straight or branched chain lower alkyl of up to 5 carbons, —$(CH_2)_4$—$NH_2$,

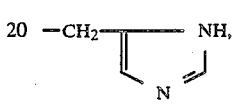

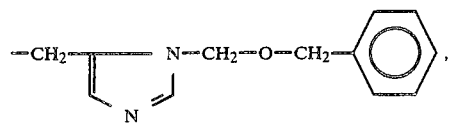

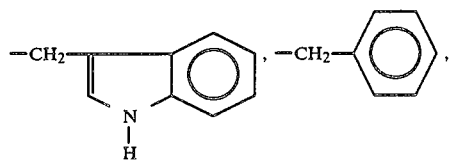

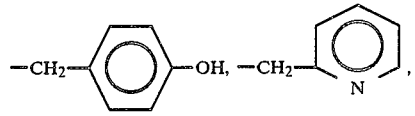

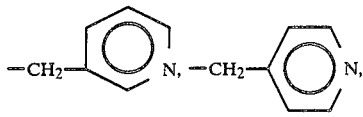

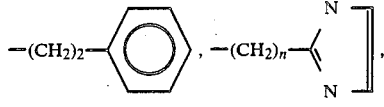

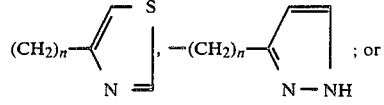

; and,

$R_5$ is straight or branched chain lower alkyl of up to 5 carbons,

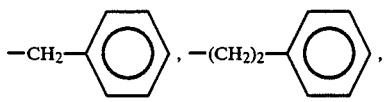

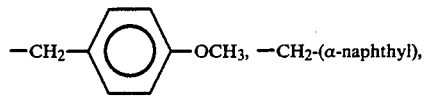

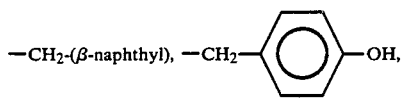

—CH₂-cyclopentyl, —CH₂-cyclohexyl, 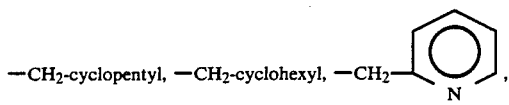

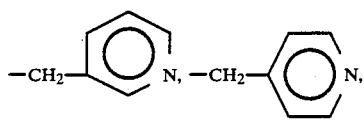

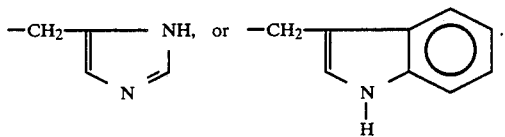

Most preferred are those compounds of formula I wherein
X—Y is

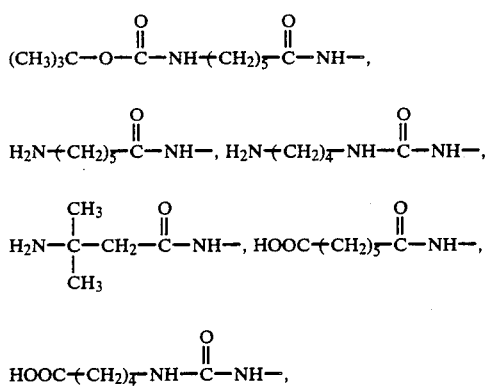

$R_1$ is

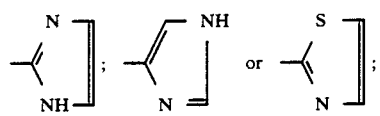

$R_3$ is

$R_4$ is

—CH₂—CH(CH₃)₂  or  —CH₂—[pyrrole]—NH; and, $R_5$ is

—CH₂—[phenyl]  or  —CH₂—[naphthyl].

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of $R_3$, $R_4$ and $R_5$ are other than hydrogen and at the carbon to which the —OH group is attached. Thus, the compounds of formula I can exist in diastereoisomeric forms or in mixtures thereof. The above-described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents. They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg, preferably about 250 to 500 mg per kg of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg, preferably about 3000 to 4000 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will now be described by the following examples, however, the invention should not be limited to the details therein.

EXAMPLE 1

[R-(R*,S*)]-6-Amino-1-oxohexyl)-L-phenylalanyl-N-[1-(cyclohexylmethyl)-2-hydroxy-2-(2-thiazolyl)ethyl]-L-leucinamide

A. N-[N-[(1,1-Dimethylethoxy)carbonyl]-L-phenylalanyl]-L-leucine, methyl ester To a solution containing N-[(1,1-Dimethylethoxy)carbonyl]-L-phenylalanine (19.89 g, 75 mmol) in dry dimethylformamide (375 mL) was added L-leucine, methyl ester, monohydrochloride (13.62 g, 75 mmol) and hydroxybenzotriazole hydrate (11.46 g, 75 mmol). The resulting mixture was cooled to 0° C. under argon and treated with diisopropylethylamine (9.69 g, 13 mL, 75 mmol) followed by 1-cyclohexyl-3-(2-morpholinoethyl) carbodiimide metho-p-toluenesulfonate (33.5 g, 75 mmol). The reaction was allowed to warm to ambient temperature overnight, then concentrated in vacuo to half volume followed by treatment with 800 ml of pH 4 phosphate buffer. A white solid that separated from solution was collected by filtration and dissolved in ethyl acetate (600 mL). The organic solution was rinsed with saturated aqueous sodium hydrogen carbonate, water and brine, then dried over anhydrous magnesium sulfate and concentrated in vacuo to give 24 g of crude product. The entire product was dissolved in hot diisopropyl ether (250 mL) and the resulting solution concentrated to about half volume and refrigerated overnight. By this method, 22.2 g of the title A compound was obtained from the first crop with an additional 1.1 g from the mother liquor, m.p. 105°–106° C.

Microanalysis calc'd for $C_{21}H_{32}N_2O_5$: C, 64.26; H, 8.22; N, 7.14; Found: C, 64.34; H, 8.41; N, 7.12.

B. N-(L-Phenylalanyl)-L-leucine, methyl ester

To a solution containing the title A compound (11 g, 28 mmol) dissolved in dry dioxane (30 mL) was added 4.5N hydrochloric acid-dioxane solution (62 mL, 280 mmol). After 3 hours at ambient temperature, the reaction was concentrated in vacuo, dried at ambient temperature at <1 mmHg pressure. The title B compound (9.9 g) was recovered as a glassy solid, m.p. 55°–58° C.

Microanalysis calc'd for $C_{16}H_{24}N_2O_3 \cdot HCl \cdot 0.66H_2O$: C, 56.40; H, 7.79; N, 8.22; Cl, 10.40; Found: C, 56.65; H, 7.87; N, 7.97; Cl, 10.04.

C. 6-[[(1,1-Dimethylethoxy)carbonyl]amino]hexanoic acid

6-Aminocaproic acid (14.4 g, 110 mmol, 1.1 eq.) was treated with sodium hydroxide (4.4 g, 110 mmol) dissolved in 11 mL of water. t-Butanol (22 mL) was added resulting in a suspension which was next treated with di-tertbutylcarbonate (21.8 g, 100 mmol) dissolved in t-butanol (22 mL). The reaction mixture, which remained a suspension, was stirred for 48 hours at room temperature, then treated with water (75 mL), giving a clear solution. The aqueous solution was then rinsed with two portions of petroleum ether (250 mL), then cooled in an ice-bath and acidified to pH 2 with solid potassium hydrogen sulfate. The acidified aqueous layer was extracted twice with portions of ethyl acetate (250 mL). The combined organic extract was rinsed with two 50 mL portions of water and brine, then dried over anhydrous magnesium sulfate and concentrated in vacuo. Trituration of the crude product (24 g) afforded 21.67 g of the title C compound, m.p. 39°–42° C.

Microanalysis calc'd for $C_{11}H_{21}NO_4 \cdot 0.1H_2O$: C, 56.68; H, 9.17; N, 6.01; Found: C, 56.68; H, 9.15; N, 6.11.

D. N-[N-[6-[[(1,1-Dimethylethoxy)carbonyl]amino]-1-oxohexyl]-L-phenylalanyl]-L-leucine, methyl ester To a suspension containing the title C compound (2.31 g, 10 mmol), the title B compound (3.40 g, 10 mmol) and hydroxybenzotriazole hydrate (1.53 g, 10 mmol) in dry tetrahydrofuran (50 mL) cooled to 0° C. under argon was added N-methylmorpholine (1.01 g, 10 mmol) followed by water-soluble carbodiimide, 1-(3-dimethylaminopropyl)-3-ethylcarbodiimide (1.91 g, 10 mmol). Cooling was removed and the reaction was allowed to warm to room temperature overnight. On the next day the reaction was treated with pH 4 phosphate buffer (150 mL) and extracted with two portions of ethyl acetate (200 mL). The combined organic extract was rinsed with saturated aqueous sodium hydrogen carbonate and brine, then dried over anhydrous magnesium sulfate and concentrated in vacuo to 4.58 g of an oil. Flash chromatography on 120 g of silica gel eluted eluted with 6:5, hexane:ethyl acetate gave 3.95 g of the title D compound.

Microanalysis calc'd for $C_{27}H_{43}N_3O_6 \cdot 0.3H_2O$: C, 63.46; H, 8.60; N, 8.22; Found: C, 63.51; H, 8.44; N, 8.21.

E.
N-[N-[6[[(1,1-Dimethylethoxy)carbonyl]amino]-1-oxohexyl]-L-phenylanyl]-L-leucine The title D methyl ester (3.6 g, 7.12 mmol) was dissolved in methanol (30 mL) and treated with 1N aqueous sodium hydroxide (7.84 mL, 7.84 mmol). After 5 hours at room temperature the reaction mixture was concentrated in vacuo and re-dissolved in water (100 mL). The aqueous solution was acidified to pH 2 with solid potassium hydrogen sulfate and the suspension of precipitated solid was stirred cold for an additional hour. The solid product was then collected by filtration and dried in vacuo to give 3.34 g of the title E compound, m.p. 142°–144° C.

Microanalysis calc'd for $C_{26}H_{41}N_3O_6$: C, 63.52; H, 8.41; N, 8.55; Found: C, 63.98; H, 8.74; N, 8.60.

F.
(S)-α-[[(1,1-Dimethylethoxy)carbonyl]amino]cyclohexanepropanoic acid

Platinum oxide catalyst (5 g) is added to a solution of N-[(1,1-dimethylethoxy)carbonyl]-L-phenylalanine (120 g, 0.452 mole) in absolute ethanol (1 l). The mixture is placed on a Parr reduction apparatus at 50 lb. pressure. The absorption of hydrogen is rapid and the hydrogen reservoir needs continued refilling. The reduction proceeds overnight and after 20 hours is completed. The mixture is filtered through Celite and concentrated in vacuo to give 124.4 g of the title F compound as a glassy solid colorless residue; $[\alpha]_D = -9.5°$ (c=1, methanol). TLC (silica gel; toluene:acetic acid, 4:1) $R_f=0.62$.

G.
(S)-α-[[(1,1-Dimethylethoxy)carbonyl]amino]-N-methoxy-N-methylcyclohexanepropanamide The title F compound (22.6 g, 83.3 mmole) is dissolved in tetrahydrofuran (250 ml) under a blanket of argon at 26°. Carbonyldiimidazole solid (16 g, 98.7 mmole) is added in portions over one minute. Moderate gas evolution begins shortly after the addition is completed. The mixture remains colorless throughout. The mixture is stirred for 30 minutes at 25° during which time it remains clear and colorless. O,N-Dimethylhydroxylamine hydrochloride (11.5 g, 118 mmole) is then added in a single portion followed immediately by triethylamine (17.5 ml, 125 mmole) in a single portion. Following the triethylamine addition a white precipitate forms. The mixture is stirred for 3 hours at 25°, after which it is poured into 1N hydrochloric acid (400 ml) and extracted with ether (3×200 ml). The colorless extracts are combined and washed with saturated sodium bicarbonate solution (2×200 ml), dried over anhydrous magnesium sulfate, and concentrated to give 24.2 g of the title G compound; $[\alpha]_D = -11.1°$ (c=7, methanol).

H.
(S)-[1-(Cyclohexylmethyl)-2-oxo-2-(2-thiazolyl)ethyl]carbamic acid, 1,1-dimethylethylethyl ester A 2.6M solution of n-butyllithium (19.5 ml, 4.78 mole) is added a solution of thiazole (4.07 g, 4.78 mmole) in tetrahydrofuran (80 ml) at −60° under argon. The reaction is stirred at −60° for 30 minutes. The product from the title G compound (7.5 g, 2.4 mmole) in tetrahydrofuran (15 ml) is added dropwise at −60° and the reaction mixture is stirred until the temperature reaches −20° (about 40 minutes). The reaction is quenched with saturated ammonium chloride (40 ml) and the product is extracted with ether (4×200 ml). The organic layer is washed with brine, dried over anhydrous magnesium sulfate, filtered and concentrated to yield 7.2 g of crude product. This material is purified by filtration through a 60 g pad of silica using a hexane:ethyl acetate (8:2) solvent system. The filtrate is concentrated in vacuo to yield 6 g of crystalline title H compound; m.p. 64°–69°. TLC (silica gel; hexane:ethyl acetate, 8:2) $R_f=0.45$.

Analysis calc'd for $C_{17}H_{26}N_2SO_3$.0.1hexane: C, 60.93; H, 7.90; N, 8.08; S, 9.24; Found: C, 61.17; H, 8.13; N, 7.95; S, 8.97.

I.
(1S,2R)-[1-(Cyclohexylmethy)-2-hydroxy-2-(2-thiazoly)ethyl]carbamic acid, 1,1-dimethylethyl ester The title H compound (2.73 g, 8.07 mmole) is dissolved in absolute ethanol (50 ml) and cooled to 5°. Sodium borohydride (0.6 g, 16.14 mmole) is added portionwise and the reaction mixture is stirred for one hour, diluted with ether (200 ml), and quenched with 1N hydrochloric acid to pH 1. The organic layer is separated, washed twice with water and brine, dried over anhydrous magnesium sulfate, and concentrated in vacuo. The two isomers are separated by flash chromatography on silica gel (300 g) eluting with ethyl acetate: hexane (3:8). The slower moving isomer is identified as the S,S configuration and the faster moving isomer is identified as the title I compound; $[\alpha]_D = -30.72°$ (c=0.55, methanol). TLC (silica gel; ethyl acetate:hexane; 1:1) $R_f=0.70$.

J.
(αR,βS)-β-Amino-α-(2-thiazolyl)cyclohexanepropanol, dihydrochloride

The title I compound (0.8 g, 2.3 mmole) is dissolved in ethyl acetate (20 ml) and hydrochloric acid is bubbled into the solution for 10 minutes, after which it is stirred at room temperature for 4 hours. The reaction mixture is concentrated to give the title J compound as a white solid.

K.
[R-(R*,S*)]-[6-[[(1,1-Dimethylethoxy)carbonyl]-amino]-1-oxohexyl]-L-phenylalanyl-N-[1-(cyclohexylmethyl)-2-hydroxy-2-(2-thiazolyl)ethyl]-L-leucinamide The title J compound (1.8 hydrochloric acid, 1 g, 3.19 mmol), hydroxybenzotriazole (0.49 g, 3.19 mmol), the title E compound (1.57 g, 3.19 mmol) and diisopropyl ethyl amine (1 ml, 5.74 mmol) were dissolved in dry tetrahydrofuran (30 ml) and 1-(3-dimethylaminopropropyl)-3-ethyl carbodiimide hydrochloride (0.61 g, 13.19 mmol) was added portionwise at 0° C. The reaction mixture was stirred under argon overnight at 0° to 12° C., concentrated in vacuo and the residue was washed twice with water and dissolved in ethyl acetate (150 ml). The ethyl acetate solution was washed with half saturated sodium hydrogen carbonate, water, brine, dried over anhydrous magnesium sulfate, filtered and concentrated in vacuo to yield 2.1 g of crude compound. This was chromatographed through 300 g of silica gel using (7:3) ethyl acetate:hexane solvent system. The appropriate fractions were combined and concentrated in vacuo to yield 1.37 g of the title K compound.

Microanalysis calc'd for $C_{38}H_{59}N_6O_6S$.0.58$H_2O$:

C, 63.00; H, 8.37; N, 9.67; S, 4.43;
Found: C, 63.02; H, 8.25; N, 9.66; S, 4.71.

L.

[R-(R*,S*)]-6-Amino-1-oxohexyl)-L-phenylalanyl-N-[1-(cyclohexylmethyl)-2-hydroxy-2-(2-thiazolyl)ethyl]-L-leucinamide The title K compound (1.63 g, 2.28 mmole) was stirred in 80 ml of ethyl acetate saturated with hydrochloric acid for 2 hours at room temperature. The solid that precipitated out was filtered, rinsed with ethyl acetate, and dried in vacuo to yield 1.34 g of the title compound.

Microanalysis calc'd for $C_{33}H_{51}N_5SO_4.1.7HCl.1.34H_2O$: C, 56.62; H, 7.97; N, 10.01; S, 4.58; Cl, 8.61; Found: C, 56.51; H, 7.92; N, 10.13; S, 4.82; Cl, 8.54.

EXAMPLE 2

[6-[[(1,1-Dimethylethoxy)carbonyl]amino]-1-oxo-hexyl]-L-phenylalanyl-N-[(1S,2R)-1-(cyclohexylmethyl)-2-hydroxy-2-(1H-imidazol-2-yl)ethyl]-L-histidinamide, 2.0 acetate salt A. (S)-(2-Cyclohexyl-1-formylethyl)carbamic acid, 1,1-dimethylethyl ester A 1M tetrahydrofuran solution of lithium aluminum hydride (85.4 ml, 85.4 mmol) was added dropwise over a period of 20 minutes to a solution of the title G compound of Example 1 (17.88 g, 56.94 mmol) in 350 ml ether at 0°. After an additional 30 minutes at 0°-2°, the reaction mixture was quenched with 250 ml 5% potassium hydrogen sulfate warmed to room temperature and the aqueous and organic layers were separated. The aqueous layer was diluted with 250 ml water and reextracted with ether (2×150 ml). The combined organic extracts were washed sequentially with 5% hydrochloric acid (150 ml), saturated aqueous sodium hydrogen carbonate (150 ml) and saturated aqueous sodium chloride (2×150 ml). After drying over anhydrous magnesium sulfate for 30 minutes, the ethereal solution was filtered through Celite and concentrated in vacuo to give 12.56 g of the title A compound. TLC, $R_f=0.63$ (silica gel, 1:1 hexane/ethyl acetate). $[\alpha]_D = -37.2°$ (c=5.59, $CH_3OH$).

B.

[(1S)-1-(Cyclohexylmethyl)-2-hydroxy-2-[1-[(phenylmethoxy)methyl]-1H-imidazol-2-yl]ethyl]carbamic acid, 1,1-dimethylethyl ester 2.5M n-Butyllithium solution in hexane (12 ml, 31 mmole) is added to a solution of 1-[(phenylmethoxy)methyl]-1H-imidazole (5.3 g, 28 mmole) in tetrahydrofuran (90 ml) at −70° under argon. After stirring for 15 minutes, the title A compound (3.6 g, 14 mmole) in tetrahydrofuran (36 ml) is added dropwise over a period of 5 minutes at a reaction temperature of −65° to −70°. After 2 hours at −70°, the bath is warmed to 0° and saturated ammonium chloride (25 ml) is added followed by ether (300 ml) and water (25 ml). The organic phase is washed with water (2×50 m) and brine, dried over mangesium sulfate, and concentrated in vacuo. The resulting crude product (8.4 g) is flash chromatographed eluting with acetone: petroleum ether (1:4) to give 580 mg of the title B compound (fast moving isomer), 370 mg of a mixed fraction, and 2 g of a slow moving isomer. TLC (silica gel; acetone:petroleum ether 1:4) $R_f=0.15, 0.10$.

Fast moving isomer; $[\alpha]_D = -21.5°$ (13 mg/ml, methanol).
Analysis calc'd for $C_{25}H_{37}N_3O_4.0.4H_2O$: C, 66.61; H, 8.45; N, 9.32; Found: C, 66.55; H, 8.39; N, 9.00.
Slower moving isomer; $[\alpha]_D = +9.1°$ (14 mg/ml, methanol).
Analysis calc'd for $C_{25}H_{37}N_3O_4.0.22H_2O$: C, 67.08; H, 8.43; N, 9.39;
Found: C, 67.08; H, 8.35; N, 9.01.

C.

$N^2$-[N-[(1,1-Dimethylethoxy)carbonyl]-L-phenylalanyl]-N-[(1S)-1-[(R)-hydroxy[1-[(phenylmethoxy)methyl]-1H-imidazol-2-yl]methyl]-2-cyclohexylethyl]-3'-[(phenylmethoxy)methyl]-L-histidinamide A solution of the title B compound (slow moving isomer) (467 mg, 1.05 mmole) in ethyl acetate (25 ml) is cooled in an ice-water bath under argon and saturated with gaseous hydrogen chloride. The stoppered reaction is kept cold for one hour and then concentrated in vacuo to give 467 mg of the amine dihydrochloride salt.

This amine salt (374 mg, 0.84 mmole) is dissolved in dimethyformamide (6 ml) along with N-[N-[(1,1-dimethylethoxy)carbonyl]-L-phenylalanyl]-1'-[(phenylmethoxy)methyl]-L-histidine (439 mg, 0.84 mole) and 1-hydroxybenzotriazole hydrate (128 mg, 0.84 mmole). The mixture is cooled under argon in an ice-water bath and treated with N-methylmorpholine (170 mg, 1.68 mmole) followed by dicyclohexylcarbodiimide (173 mg, 0.84 mmole). The stopped reaction mixture is refrigerated overnight, then filtered and extracted with ethyl acetate. The organic solution is rinsed with water, saturated sodium bicarbonate, water, and brine, dried over magnesium sulfate, and concentrated in vacuo to 730 mg of crude product. Flash chromatography eluting with chloroform:methanol:concentrated ammonia (30:2:0.05) gives 271 mg of the title C compound; $[\alpha]_D = -8.7°$ (c=1, methanol). TLC (silica gel; chloroform:methanol:concentrated ammonia, 30:2:0.05) $R_f=0.14$.

Analysis calc'd for $C_{48}H_{61}N_7O_7$: C, 67.98; H, 7.25; N, 11.56; Found: C, 67.80; H, 7.27; N, 11.44.

D.

$N^2$-(L-Phenylalanyl)-N-[(1S,2R)-2-cyclohexyl-1-hydroxy[1-[(phenylmethoxy)methyl]-1H-imidazol-2-yl]-methyl]ethyl]-$N^3$-[(phenylmethoxy)methyl[-L-histidinamide, trihydrochloride salt A solution of the title C compound (7.63 g, 9.0 mmole) in ethyl acetate (325 ml) is cooled in an ice-water bath under argon and then saturated with gaseous hydrogen chloride. The mixture is stoppered and stirred cold for 30 minutes, then the bath is removed and the mixture is allowed to warm to 25° over 60 minutes. Removal of the solvents in vacuo followed by drying of the colorless solid product in vacuo gives 7.64 g of the title D compound as a trihydrochloride salt.

E.

[R-(R*,S*)]-[6-[[1,1-Dimethylethoxy)carbonyl]amino]-1-oxohexyl]-L-phenylalanyl-N-[1-(cyclohexylmethyl)-2-hydroxy-2-[1-[(phenylmethoxy)methyl]-1H-imidazol-2-yl]ethyl]-3-[(phenylmethoxy)methyl]-L-leucinamide To a suspension containing the title C compound of Example 1 (0.462 g, 2 mmol), the title D compound of this Example (1.79 g, 2 mmol), and hydroxybenzotriazole hydrate (0.306 g, 2 mmol) in dry tetrahydrofuran (15 mL) cooled to 0° C. under argon was added N-methylmorpholine (0.607 g, 6 mmol) followed by dicyclohexylcarbodiimide (0.413 g, 2 mmol). After the addition of N-methylmorpholine, dimethylformamide (1 mL) was added to the reaction mixture. Cooling was removed and the reaction was allowed to warm to room temperature overnight. On the next day the reaction was filtered, then partioned between ethyl acetate and water. The combined organic extract was rinsed with saturated aqueous sodium hydrogen carbonate and brine, then dried over anhydrous magnesium sulfate and concentrated in vacuo to give 1.98 g of an oil. Flash chromatography on silica gel eluted with 200:20:6:11, ethyl acetate:pyridine:HOAc:water gave 0.963 g of the title E compound.

Microanalysis calc'd for $C_{54}H_{72}N_8O_8\cdot 1.09H_2O$: C, 66.12; H, 7.62; N, 11.43; Found: C, 66.00; H, 7.60; N, 11.28.

F. [6-[[(1,1-Dimethylethoxy)carbonyl]amino]-1-oxo-hexyl]-L-phenylalanyl-N-[(1S,2R)-1-(cyclohexylmethyl)-2-hydroxy-2-(1H-imidazol-2-yl)ethyl]-L-histidinamide, 2.0 acetate salt The protected title E compound (0.910 g, 0.947 mmol) was dissolved in a mixture of methanol (20 mL) and water (3.1 mL) to which had been added 1N aqueous hydrochloric acid (1.89 mL). The resulting solution was then put under an atmosphere of hydrogen and 150 mg of 20% palladium hydroxide on carbon was added. After 48 hours, the reaction mixture was filtered and concentrated in vacuo. The crude product was purified by flash chromatography on 80 g of silica gel eluted with 90:20:2.5:1, chloroform:methanol:water:HOAc gave 282 mg of the title compound obtained as a bis-acetic acid salt, m.p. 155°–193° C.

Microanalysis calc'd for $C_{38}H_{56}N_8O_6\cdot 2C_2H_4O_2\cdot 2.8\text{-}H_2O$: C, 56.59; H, 7.87; N, 12.57; Found: C, 56.57; H, 7.48; N, 12.88.

EXAMPLE 3

[R-(R*,S*)]-(6-Amino-1-oxohexyl)-L-phenylalanyl-N-[1-(cyclohexylmethyl)-2-hydroxy-2-(1H-imidazol-2-yl)ethyl]-L-histidinamide, trihydrochloride The title compound of Example 2 (0.17 g, 0.19 mmole) was dissolved in acetic acid (5 ml) saturated with hydrochloric acid and stirred at room temperature for 2 hours. The reaction mixture was concentrated in vacuo and the concentrate was washed twice with ethyl acetate to give a granular solid which was dissolved in water (10 ml). The solution was filtered through millipore, lyophilized and dried over phosphorus pentoxide to yield 0.14 g of the title compound.

Analysis calc'd for $C_{33}H_{48}N_8O_4\cdot 3.45HCl\cdot 4.35H_2O$: C, 48.07; H, 7.30; N, 13.59; Cl, 14.84; Found: C, 48.24; H, 7.07; N, 13.84; Cl, 14.97.

EXAMPLES 4–32

Following the procedures of the Examples and as outlined above, additional compounds within the scope of this invention can be prepared having the formula

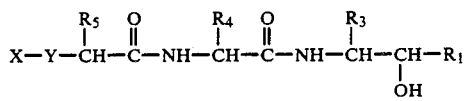

wherein the substituents are as defined below.

| Ex. No. | X | Y | R5 | R4 | R3 | R1 |
|---|---|---|---|---|---|---|
| 4 | H2N—(CH2)5—C(=O)— | —NH— | H3CO—⟨Ph⟩—CH2 | (CH3)2CH—CH2— | ⟨Cyclohexyl⟩—CH2 | imidazol-2-yl (NH/N) |
| 5 | " | " | " | " | " | thiazol-2-yl (S/N) |
| 6 | " | " | ⟨Ph⟩—CH2 | imidazol-4-ylmethyl (H-N, N—CH2—) | " | imidazol-2-yl (NH/N) |
| 7 | " | " | ⟨naphthyl⟩—CH2 | (CH3)2CH—CH2— | " | thiazol-2-yl (S/N) |
| 8 | HO2C—(CH2)5—C(=O)— | " | ⟨Ph⟩—CH2— | " | " | ⟨Cyclohexyl⟩—CH2— |

-continued

| Ex. No. | X | Y | R5 | R4 | R3 | R1 |
|---|---|---|---|---|---|---|
| 9 | (CH$_3$)$_2$C(NH$_2$)-CH$_2$-C(=O)- | " | " | " | " | " |
| 10 | H$_2$N-C(=NH)-HN-(CH$_2$)$_5$-C(=O)- | " | " | " | " | " |
| 11 | H$_2$N-C(=O)-NH-(CH$_2$)$_5$-C(=O)- | " | " | " | " | " |
| 12 | H$_2$N-(CH$_2$)$_5$-C(=O)- | " | " | thiazolyl-CH$_2$- | " | imidazolyl (NH) |
| 13 | " | " | phenyl-CH$_2$- | " | cyclohexyl-CH$_2$- | thiazolyl |
| 14 | " | " | naphthyl-CH$_2$- | imidazolyl(NH)-CH$_2$- | " | imidazolyl (NH) |
| 15 | " | " | " | " | " | thiazolyl |
| 16 | HO$_2$C-(CH$_2$)$_5$-C(=O)- | " | phenyl-CH$_2$- | " | " | imidazolyl (NH) |
| 17 | " | " | " | " | " | imidazolyl (NH) |
| 18 | " | " | " | " | " | thiazolyl |
| 19 | (CH$_3$)$_2$C(NH$_2$)-CH$_2$-C(=O)- | " | " | " | " | imidazolyl (NH) |
| 20 | " | " | " | " | " | imidazolyl (NH) |

| Ex. No. | X | Y | R₅ | R₄ | R₃ | R₁ |
|---|---|---|---|---|---|---|
| 21 | " | " | Ph-CH₂- | " | " | thiazoline (S,N ring) |
| 22 | H₂N-C(=NH)-HN-(CH₂)₅-C(=O)- | " | " | " | " | imidazoline (NH,N ring) |
| 23 | " | " | " | " | " | thiazoline (S,N ring) |
| 24 | " | " | " | " | " | imidazole (NH,N ring) |
| 25 | H₂N-(CH₂)₄-NH-C(=O)- | " | " | (CH₃)₂CH-CH₂- | " | thiazoline (S,N ring) |
| 26 | " | " | " | imidazole-CH₂- | " | " |
| 27 | " | " | " | " | " | imidazoline (NH,N ring) |
| 28 | " | " | " | " | " | imidazole (NH,N ring) |
| 29 | HOOC-(CH₂)₄-NH-C(=O)- | " | Ph-CH₂- | (CH₃)₂CH-CH₂- | " | thiazoline (S,N ring) |
| 30 | " | " | " | imidazole-CH₂- | " | imidazoline (NH,N ring) |
| 31 | " | " | " | " | " | imidazole (NH,N ring) |
| 32 | " | " | " | " | " | thiazoline (S,N ring) |

What is claimed is:

1. A compound having the formula

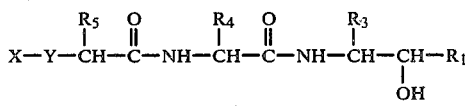

including pharmaceutically acceptable salts thereof, wherein Y is —NH—, provided that:
when Y is —NH—, X is,

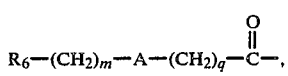

and, further wherein

R₁ is a fully saturated, partially saturated, or unsaturated monocyclic N-heterocyclic ring of 5 or 6 atoms containing at least one N atom or a bicyclic ring in which such N-heterocyclic ring is fused to a benzene ring, wherein the N-heterocyclic ring can also include an O or S atom or up to three additional N atoms and further wherein the N-heterocyclic ring is attached to

by way of an available carbon atom and, an available N atom in the N-heterocyclic ring can be substituted with an N-protecting group such as

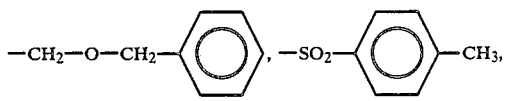

or 2,4-dinitrophenyl, or loweralkyl,

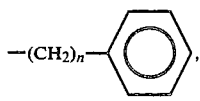

or —(CH₂)$_n$-cycloalkyl;

R₂ is

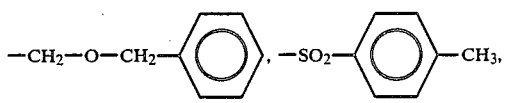

2,4-dinitrophenyl, hydrogen, lower alkyl,

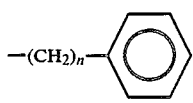

or —(CH₂)$_n$-cycloalkyl;

R₃ and R₅ are independently selected from hydrogen, lower alkyl, halo substituted lower alkyl, —(CH₂)$_n$-aryl, —(CH₂)$_n$—OH, —(CH₂)$_n$—O-lower alkyl, —(CH₂)$_n$—NH₂, —(CH₂)$_n$—SH, —(CH₂)$_n$—S-lower alkyl, —(CH₂)$_n$—O—(CH₂)$_g$—OH, —(CH₂)$_n$—O—(CH₂)$_g$—NH₂, —(CH₂)$_n$—S—(CH₂)$_g$—OH,

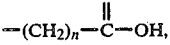

—(CH₂)$_n$—S—(CH₂)$_g$—NH₂,

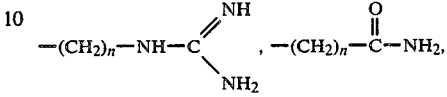

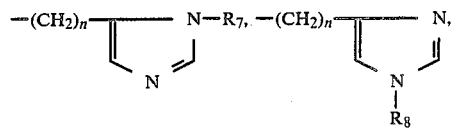

and —(CH₂)$_n$-cycloalkyl;

R₄ is selected from hydrogen, lower alkyl, halo substituted lower alkyl, —(CH₂)$_n$-aryl, —(CH₂)$_n$—OH, —(CH₂)$_n$—O-lower alkyl, —(CH₂)$_n$—NH₂, —(CH₂)$_n$—SH, —(CH₂)$_n$—S-lower alkyl, —(CH₂)$_n$—O—(CH₂)$_g$—OH, —(CH₂)$_n$—O—(CH₂)$_g$—NH₂, —(CH₂)$_n$—S—(CH₂)$_g$—OH,

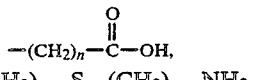

—(CH₂)$_n$—S—(CH₂)$_g$—NH₂,

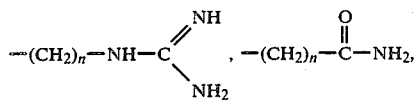

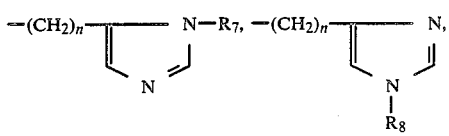

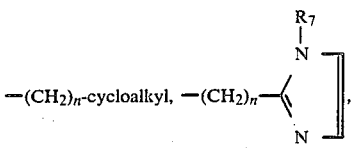

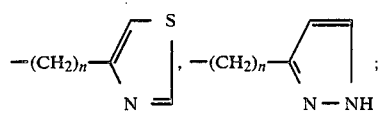

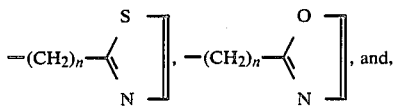

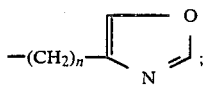

R₆ is

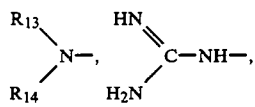

R₆', R₆'', R₆''', R₁₃ and R₁₄ are independently selected from hydrogen, alkyl, aryl, arylalkyl and cycloalkyl;
m, m', m'' and m''' are zero or an integer from 1 to 5;
n is an integer from 1 to 5;
p and p' are zero or 1;
g is an integer from 2 to 5;
q is an integer from 0 to 7;
R₇ is

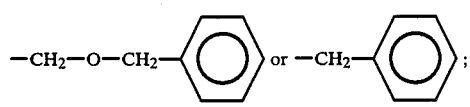

R₈ is 2,4-dinitrophenyl,

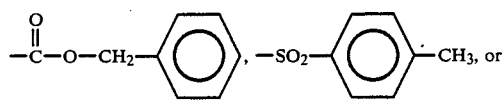

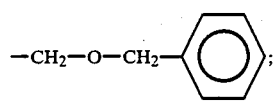

R₉ is hydrogen, lower alkyl, —(CH₂)ₙ, or —(CH₂)ₙ-cycloalkyl; and,
A and A' are independently a single bond or

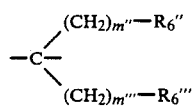

2. A compound of claim 1 wherein R₁ is

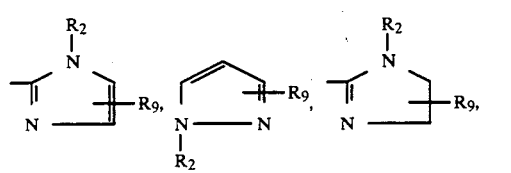

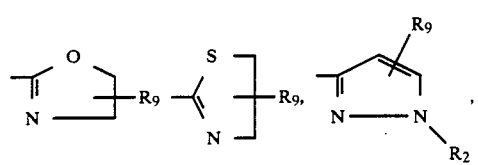

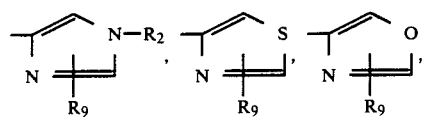

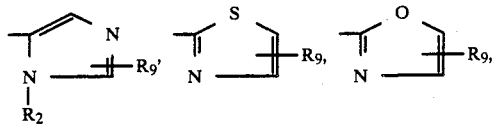

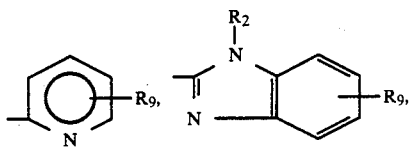

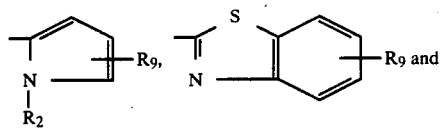

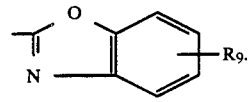

3. A compound in accordance with claim 1 wherein X—Y is

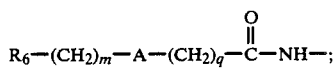

R₁ is

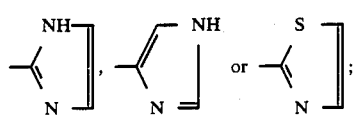

R₃ is straight or branched chain lower alkyl of 3 to 5 carbons, —(CH₂)ₙ-cyclopentyl, —(CH₂)ₙ-cyclohexyl, or

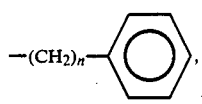

wherein n is an integer from 1 to 3;
R₄ is hydrogen, straight or branched chain lower alkyl of up to 5 carbons, —(CH₂)₄—NH₂,

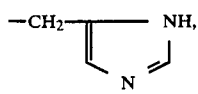

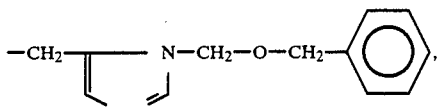

-continued
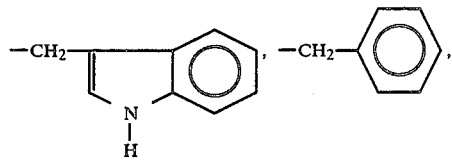
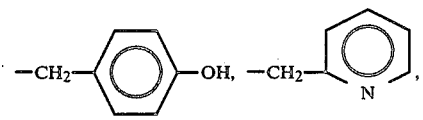
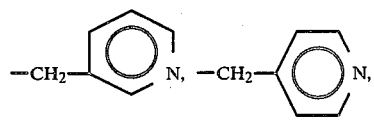
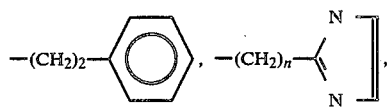
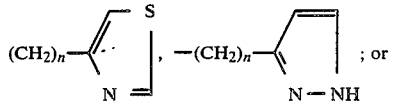
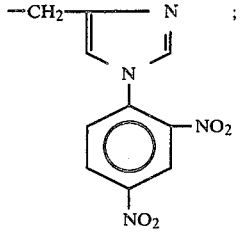
$R_5$ is straight or branched chain lower alkyl of up to 5 carbons,
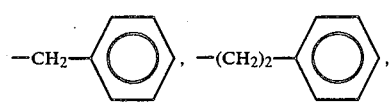
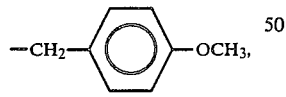
—CH$_2$—(α-naphthyl), —CH$_2$—(β-naphthyl),
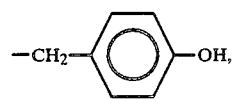
—CH$_2$-cyclopentyl, —CH$_2$-cyclohexyl,
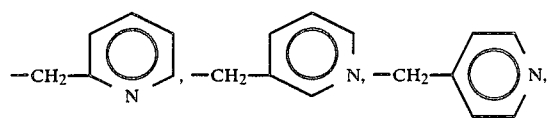
-continued
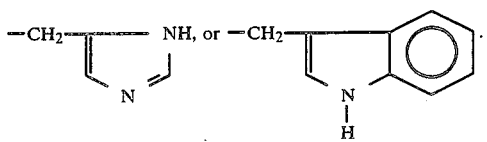
4. A compound in accordance with claim 1 wherein X—Y is
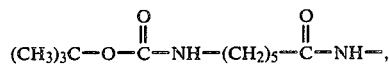
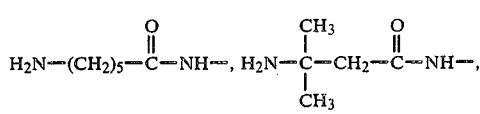
$R_1$ is
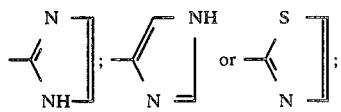
$R_3$ is
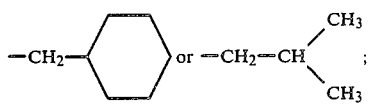
$R_4$ is
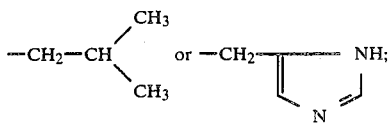
and,
$R_5$ is
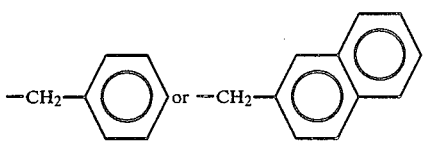
5. A compound of claim 1 wherein $R_1$ is
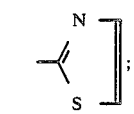
$R_3$ is R4 is

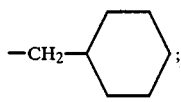

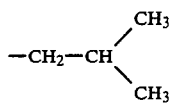

R5 is

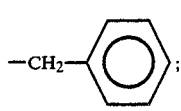

Y is —NH—; and,
X is

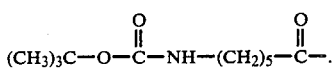

6. A compound of claim 1 wherein
R1 is

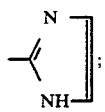

R3 is

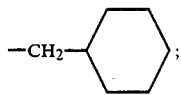

R4 is

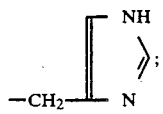

R5 is

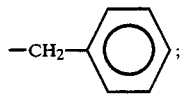

Y is —NH—; and,
X is

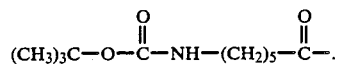

7. A compound of claim 1 wherein
R1 is

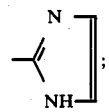

R3 is

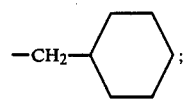

R4 is

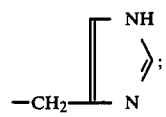

R5 is

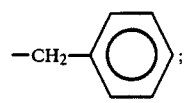

Y is —NH—; and,
X is

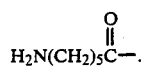

8. A compound of claim 1 having the name [R-(R*,S*)]-6-amino-1-oxohexyl)-L-phenylalanyl-N-[1-(cyclohexylmethyl)-2-hydroxy-2-(2-thiazolyl)-ethyl]-L-leucinamide.

9. A compound of claim 1 having the name [6-[[(1,1-dimethylethoxy)carbonyl]amino]-1-oxo-hexyl]-L-phenylalanyl-N-[(1S,2R)-1-(cyclohexyl-methyl)-2-hydroxy-2-(1H-imidazol-2-yl)ethyl]-L-histidinamide, 2.0 acetate salt.

10. A compound of claim 1 having the name [R-(R*,S*)]-(6-amino-1-oxohexyl)-L-phenylalanyl-N-[1-(cyclohexylmethyl)-2-hydroxy-2-(1H-imidazol-2-yl)ethyl]-L-histidinamide, trihydrochloride.

11. A composition for treating hypertension in a mammalian species comprising a pharmaceutically acceptable carrier and an anti-hypertensively effective amount of a compound of claim 1.

12. A method of treating hypertension in a mammalian species which comprises administering an anti-hypertensively effective amount of the composition of claim 11.

* * * * *